(12) United States Patent
Grossman

(10) Patent No.: US 8,763,796 B2
(45) Date of Patent: Jul. 1, 2014

(54) DENTAL FLOSS DISPENSER AND METHOD OF OPERATION THEREOF

(71) Applicant: Victor A. Grossman, Staten Island, NY (US)

(72) Inventor: Victor A. Grossman, Staten Island, NY (US)

(*) Notice: Subject to any disclaimer, the term of this patent is extended or adjusted under 35 U.S.C. 154(b) by 0 days.

(21) Appl. No.: 13/735,093

(22) Filed: Jan. 7, 2013

(65) Prior Publication Data

US 2013/0118940 A1    May 16, 2013

Related U.S. Application Data

(63) Continuation of application No. 12/753,131, filed on Apr. 2, 2010, now Pat. No. 8,348,050.

(60) Provisional application No. 61/166,595, filed on Apr. 3, 2009.

(51) Int. Cl.
   *A61C 15/04*    (2006.01)

(52) U.S. Cl.
   CPC .................................. *A61C 15/043* (2013.01)
   USPC ........................... 206/63.5; 206/388; 132/324

(58) Field of Classification Search
   CPC ..................................................... A61C 15/043
   USPC ....................... 206/63.3, 63.5, 368, 369, 388; 132/321–324
   See application file for complete search history.

(56) References Cited

U.S. PATENT DOCUMENTS

| | | | | | |
|---|---|---|---|---|---|
| 2,530,292 | A | * | 11/1950 | Crook | 206/315.11 |
| 2,538,920 | A | * | 1/1951 | Shumann | 383/106 |
| 3,323,442 | A | * | 6/1967 | Rader | 383/103 |
| 4,579,221 | A | * | 4/1986 | Corella | 206/63.3 |
| 4,693,365 | A | * | 9/1987 | Corella | 206/63.3 |
| 4,712,572 | A | * | 12/1987 | Hovel, III | 132/321 |
| 4,852,728 | A | * | 8/1989 | Court | 206/63.5 |
| 4,986,289 | A | * | 1/1991 | McWhorter | 132/323 |
| 5,119,941 | A | * | 6/1992 | Lepie | 132/323 |
| 5,322,077 | A | * | 6/1994 | Corella | 132/323 |

* cited by examiner

*Primary Examiner* — Luan K Bui

(57) ABSTRACT

A dispenser including a first sheet defining at least part of one or more cavities; a second sheet defining at least another part of the one or more cavities; a plurality of pull covers attached to at least one of the first sheet and the second sheet; and a plurality of floss portions each located in a corresponding cavity of the one or more cavities, wherein when a pull cover of the plurality of pull covers is separated from the first sheet or the second sheet, a corresponding floss portion of the plurality of floss portions is removed, from a corresponding cavity of the plurality of the one or more cavities. One or more of the floss portions may be attached to, or formed integrally with, a corresponding pull cover of the plurality of pull covers. A weakened area may delineate a pull cover.

20 Claims, 23 Drawing Sheets

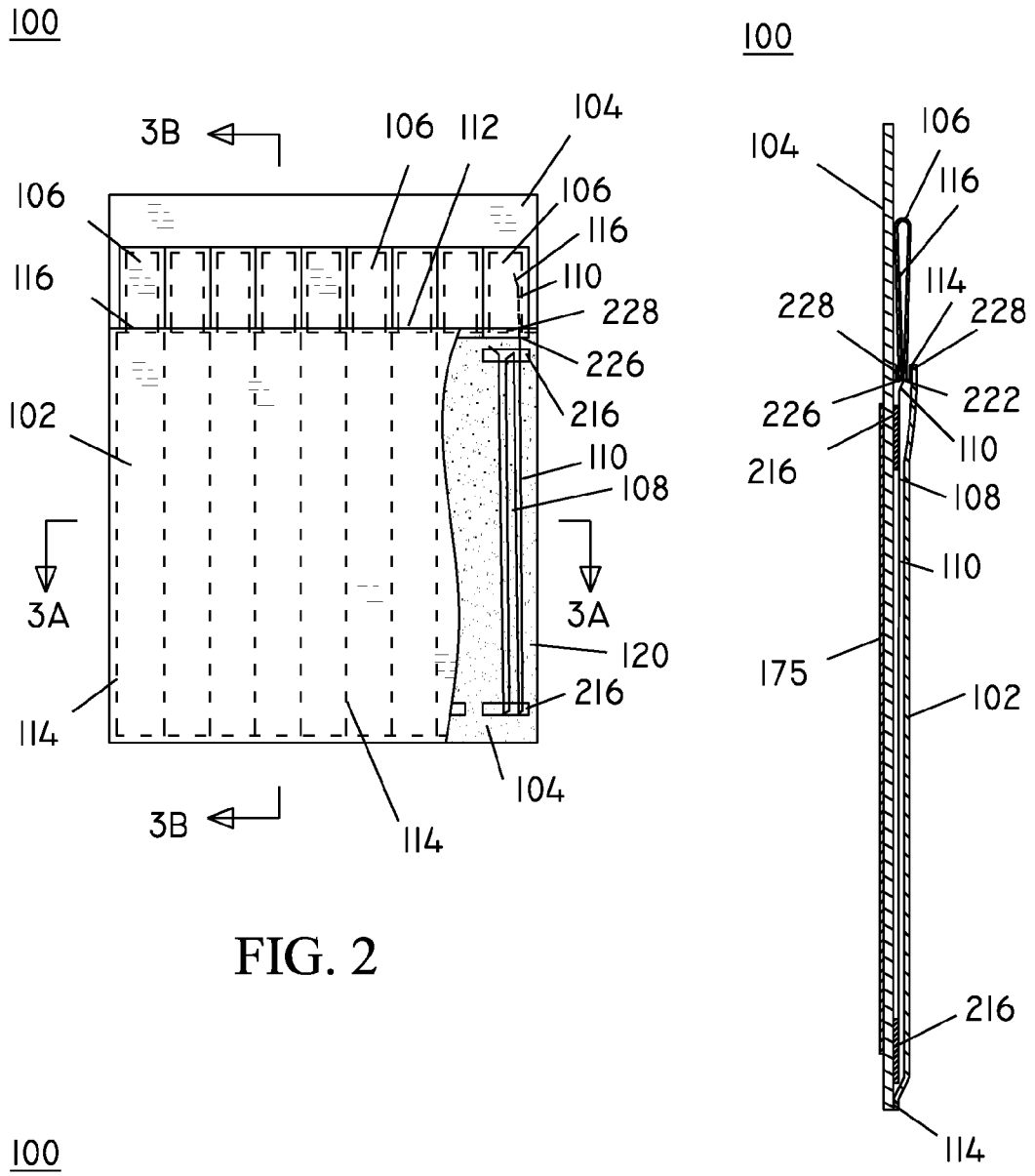
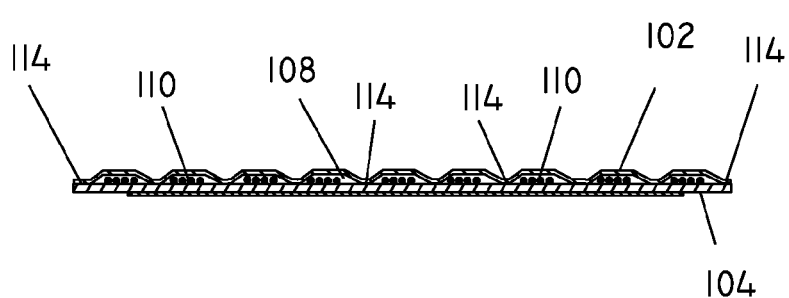
FIG. 2
FIG. 3B
FIG. 3A

DENTAL FLOSS DISPENSER AND METHOD OF OPERATION THEREOF

CROSS REFERENCE TO RELATED APPLICATIONS

This application is a continuation of U.S. patent application Ser. No. 12/753,131, filed Apr. 2, 2010, and issued as U.S. Pat. No. 8,348,050 which claims priority to U.S. Provisional Application Ser. No. 61/166,595, filed Apr. 3, 2009, entitled "Dental Floss Dispenser and Method of Operation Thereof," the contents of each of which are incorporated herein by reference in its their entirety.

TECHNICAL FIELD

The present system relates generally to dental floss dispensers and, more particularly, to a sanitary dental floss dispensing system that can dispense individual floss portions, and a method of operation thereof.

BACKGROUND

Typically, dental floss dispensers comprise a spool of floss placed, in a container. The dental floss commonly passes through an opening and is cut using a cutler which is located proximate to the opening. To dispense floss, a user must unwind a section of the floss and thereafter cut the floss using a cutter on the package which is inconvenient. Further, contaminates may pass through opening and contaminate the floss. This is more likely to occur when a user places a container in an unsanitary environment such as, for example, a bathroom and/or a wallet. Accordingly, there is a need for a sanitary dental floss container which can dispense individual floss portions in a sanitary manner.

SUMMARY

Accordingly, the present system provides a sanitary dental floss container which can dispense individual floss portions in a sanitary manner.

The present systems, methods, apparatuses, and devices (hereinafter system unless context indicates otherwise) overcomes the disadvantages of conventional systems and devices.

According to one illustrative embodiment., there is disclosed a dispenser which may include a first sheet defining at least part of one or more cavities; a second sheet defining at least another part of the one or more cavities; a plurality of pull covers (e.g., pull tabs) attached to (i.e., coupled to) at least one of the first sheet and the second sheets; and a plurality of floss portions (e.g., dental floss) each located in a corresponding one of the one or more cavities, wherein when a pull cover of the plurality of pull covers is separated from the first sheet and/or the second sheet, the corresponding floss portion is removed from the corresponding cavity of the one or more cavities. The one or more floss portions of the plurality of floss portions may be attached to a corresponding pull cover of the plurality of pull covets. One or more pull covers of the plurality of pull covers may include a first portion and a second portion and a fold separating the first portion and the second portion.

At least a part of a floss portion of the plurality of floss portions may be located between the first and second portions of a corresponding pull cover of the plurality of pull covers. The dispenser may further include a weakened portion at which a corresponding pull cover of the one or more pull covers separates from the upper sheet and/or the lower sheet and/or which may define an end of a corresponding pull cover of the one or more pull covers. Further, a reflective surface may be located adjacent to a major surface of the first sheet or the second sheet. The dispenser may further include a biasing member to bias one or more of the first sheet and the second sheet, the biasing member may be coupled to one or more of the first sheet and the second sheet. The biasing member may include a spring, a. rigid or semi rigid member, etc., which may hold the first and/or second sheets in a desired position. For example, the biasing member may include a polymer having a rigidity similar to that of a credit card. The dispenser may further include an enclosure such as, for example, a dispending pack.

According to yet a further aspect of the present system there is disclosed a method for manufacturing a dispenser, the method including one or more acts of: defining at least one or more cavities using a first sheet; defining at least another part of the one or more cavities using a second sheet; attaching one or more pull covers to at least one of the first sheet and the second sheets: and locating a floss portion of a plurality of floss portions in each of the one or more cavities, wherein when a pull cover of the one or more pull covers is separated from one or more of the first sheet and the second sheet, the corresponding floss portion of the plurality of floss portions is removed from the corresponding cavity of the one or more cavities.

The method may further include an act of attaching a floss portion of the plurality of floss portions to a corresponding pull cover of the one or more pull covers. The method may further include an act of folding at least one of the one or more pull covers so as to form a first part and a second part situated on opposite sides of the fold. The method may also include an act of locating at least a part of a floss portion of the plurality of floss portions between the first and second parts of a corresponding pull cover of the one or more pull covers. The method may further include an act of forming weakened portion at which a corresponding pull cover of the one or more pull covers separates from the upper sheet and/or the lower sheet and/or which may define an end of a corresponding pull cover of the one or more pull covers. The method may further include an act of locating a reflective surface adjacent to a major surface of the first sheet or the second sheet The method may also include an act of biasing one or more of the first sheet of the second sheet using a biasing member coupled to one or more of the first sheet and the second sheet. Further, the method may include an act of enclosing at. least one or more of the first sheet, the second sheet and the pall cover in an enclosure.

According to yet a further aspect of the present system, there is disclosed a method to dispense floss from a dispenser, the method may include one or more acts of: separating a first pull cover from the dispenser to remove a first floss portion attached to the first pull cover; and separating a further pull cover from the dispenser to dispense a further floss portion attached to the further pull cover. The method may also include an act of separating another pull cover for the dispenser to dispense yet another floss portion. Further, according to the method, each of the first floss portion, the further portion of floss portion, and the another floss portion may each be removed from a separate cavity of a plurality of cavities.

According to yet another aspect of the present system, there is disclosed a dispenser which may include: a plurality of floss portions; at least one sheet forming at least part of a plurality of cavities, one or more cavity of the plurality of cavities being configured to receive a corresponding floss portion of the plurality of floss portions; and a pull cover attached to a corresponding floss portion of the plurality of floss portions. The at least one sheet may include a corrugated cardboard.

Dispensers according to the present system and methods may include various shapes and sizes so that they may be desired by children. Further, the dispensers may include advertising and/or promotional text and/or graphics. Further, a radio frequency identification (RFID) device including a controller may be included for identification, etc. Accordingly, RFID device may transmit a message to an RFID reader to inform a user that the dispenser is running low on floss. The RFID device may be activated when a certain pull tab is removed. Further, the dispensers according to the present system may include a display device such as, for example, a light emitting diode (LED) to inform a user of a status (e.g., running low) and/or to provide a lighting function In low fight conditions (e.g., to aid vision of a user during a flossing operation). Accordingly, a power source and/or a switch may be provided to operate the LED when desired by a user.

BRIEF DESCRIPTION OF THE DRAWINGS

These and other features, aspects, and advantages of the apparatus., systems and methods of the present invention will become better understood from the following description, appended claims, and accompanying drawings where:

FIG. 2 is a partially cutaway front view of a dispensing system shown in FIG. 1;

FIG. 3A is a cutaway illustration of the dispensing system taken along lines 3A-3A of FIG. 2;

FIG. 3B is a cutaway illustration of the dispensing system taken along lines 3B-3B of FIG. 2;

DETAILED DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof and in which are shown by way of illustration specific embodiments in which the described systems and methods may be practiced. These embodiments are described in sufficient detail to enable those skilled in the art to practice the presently disclosed systems and methods, and it is to be understood that, other embodiments may be utilized and that structural and logical changes may be made without departing from the spirit and scope of the present system.

The following detailed description is therefore not to be taken in a limiting sense, and the scope of the present system is defined only by the appended claims. Moreover, for the purpose of clarity, detailed descriptions of certain, features will not be discussed when they would be apparent to those with skill in the art so as not to obscure the description of the present system.

In one embodiment, there is provided system, apparatus, device, and/or method for forming a dispenser including a first sheet defining at least part of one or more cavities: a second sheet defining at least another part of the one or more cavities; a pull cover attached to at least one of the first sheet and the second sheets; and a portion of floss located in each of the one or more cavities, wherein when the pull cover is separated from the first sheet or the second sheet, the corresponding portion of floss is removed from the corresponding cavity of the plurality of cavities. The floss may be attached to, or formed integrally with, the pull cover. A weakened area may delineate the pull cover. Accordingly, sanitary floss strips may be provided and user convenience can be enhanced.

Figure 1:
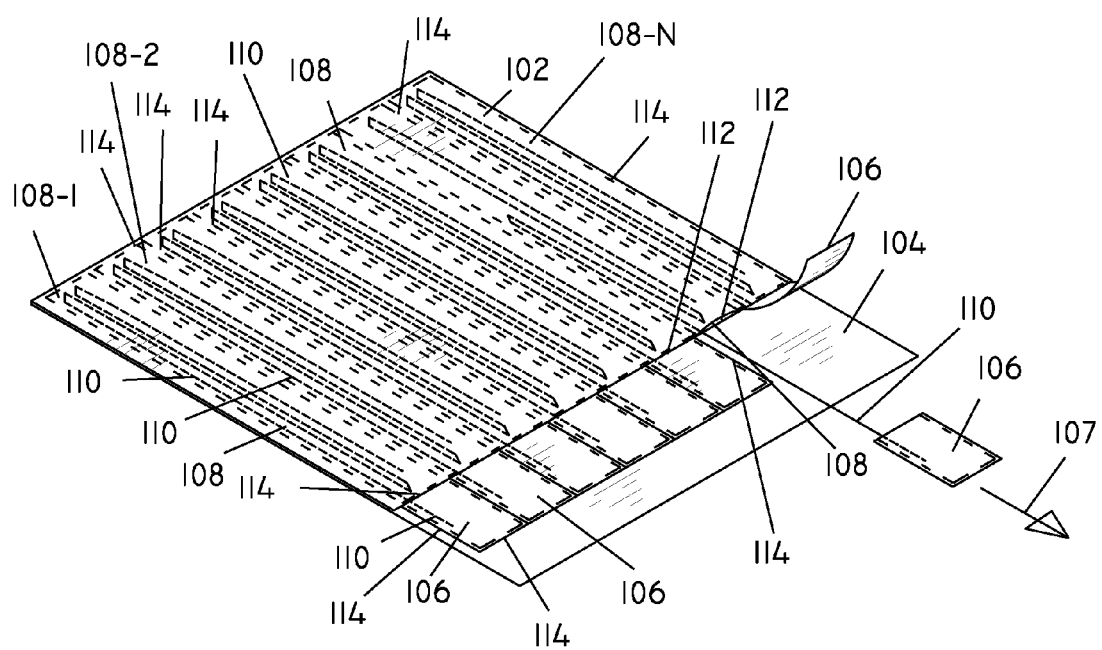
FIG. 1 is a perspective front view of a dispensing system according to an embodiment of
the present system.

FIG. 1 is a perspective front view of a dispensing system 100 according to an embodiment of the present system. The dispensing system 100 may include one or more of a upper sheet 102, a lower sheet 104, a plurality of pull tabs 106, a plurality of cavities 108 (or 108-1-108-N), and a plurality of floss portions 110.

The upper and lower sheets 102 and 104, respectively, form at least part of portions of the plurality of cavities 108. Each of the plurality of cavities 108-x is preferably separate from adjacent cavities of the plurality of cavities 108, and may include an opening 112 through which one or more of the floss portions 110 may pass when a pull tab 106 is removed from the upper and/or lower sheets 102 and 104, respectively.

The upper and lower sheets 102 and 104, respectively, may be attached to each other to form one or more cavities 108-x of the plurality of cavities 108 using any suitable method. For example, an adhesive, a cohesive, weld, a glue, a bond, combinations thereof, etc., may be used to couple the upper and lower sheets 102 and 104, respectively, to each other at one or more locations. For example, one or more cavities 108 may be defined, at least in part, by seal 114 which may be formed by bonding the upper sheet 102 to the lower sheet 104. Further, one or more intermediary members may be situated and/or attached to a major surface of either or both of the upper and lower sheets 102 and 104, respectively. The one or more intermediary members may include a semi rigid member, a stiffening member, a holding member (e.g., to hold and/or support one or more individual floss portions 110), etc.

Each of the floss portions 110 may be folded, wrapped, or otherwise arranged so that a sufficient length of floss 110 may be stored within a respective cavity 108. For example, according to an embodiment a length of a portion of floss 110 may be greater than twelve inches. However, other lengths (e.g., shorter or longer) axe also envisioned.

FIG. 2 is a partially cutaway front view of a dispensing system shown in FIG. 1. The upper sheet 102 has been partially cutaway to reveal a portion of a cavity 108. The upper sheet 102 may be attached to the lower sheet 104 using a cohesive 120 which may coat opposing major surfaces of the upper sheet 102 and/or the lower sheet 104. However, it is also envisioned that other bonding methods may be used (e.g., adhesives, welds, etc.). The individual floss portions 110 may be held in place (e.g., at folds, etc.) by the cohesive 120 and/or pads 216. Pads 216 may be placed in each of the cavities 108 and may include adhesive to position the individual floss portions 110 during assembly. Further, when removing the individual portions of floss 110 from corresponding cavities 108. the cohesive 120 and/or the adhesive pads 216 may provide a desired resistance to the individual portions of floss 110 such that bunching up may be prevented. Although pads 216 are shown on a major surface of the lower sheet 104, they may also be located on a major surface of the upper sheet 102. in yet other embodiments, the pads may include any type of restraining member. For example, the pads may include a film (e.g., paper, plastic, etc.) which may be attached to either or both of the upper sheet 102 and/or the lower sheet 104. A portion of an individual portion of floss 110 may be threaded, wrapped around and/or otherwise attached to a corresponding pad. Accordingly, during removal of an individual portion of floss 110, the corresponding section of floss may pull away from and/or rip the corresponding pad. Accordingly, a desired resistance may be provided and/or bunching of the portions of floss as they are removed from a corresponding cavity may be reduced and/or prevented. Further, it is also envisioned that individual portions of floss 110 may be mounted in wrapper (e.g., a film wrapper) and thereafter attached to the upper sheet 102 and/or the lower sheet 104. The film wrapper may also form a part of a corresponding pull tab. A portion of floss 110 may be attached to a corresponding pull tab 106 at bond. 116.

FIG. 3A is a cutaway illustration of the dispensing system 100 taken along lines 3A-3A of FIG. 2. Seals 114 may include a bond formed using any suitable method such as for example, opposing cohesive layers which may be located on opposing major surfaces of the upper sheet 102 and/or the lower sheet 104.

FIG. 3B is a cutaway illustration of the dispensing system 100 taken along lines 3B-3B of FIG. 2. The pull tab 106 may include one or more folds 222 and 226 and may be attached to a portion of floss 110. The folds 226 may define appendages 228 which may be attached to adjacent portions of the upper sheet 102 and/or the lower sheet 104 using any suitable attachment method. For example, suitable attachment methods may include adhesive and/or cohesive layers or other suitable bonding methods. Although the pull tab 106 is folded about a portion of floss 110, it is also envisioned that the portion of floss may also be attached to any surface of an unfolded portion of the pull cover. An optional reflective surface 175 may be deposited upon and/or attached to a major surface of either or both of the upper sheet 102 and/or the lower sheet 104. The reflective surface may be used by a user as a mirror. The reflective surface 175 may include a vapor deposited aluminum, etc. which may be deposited directly upon the upper sheet 102 and/or the lower sheet 104. Further, the reflective surface may include a substrate such as, for example, a film (e.g., a Mylar™ film, etc.). The strength and/or rigidity of the upper sheet 102 and/or the lower sheet 104 may differ from each other. For example, the lower sheet may be formed from a semi-rigid film so as to enhance rigidity. The dispensing system 100 may be shaped and/or sized such that it may be inserted in a user's wallet or handbag. For example, the shape and/or size of the dispenser may be similar to a conventional credit card, if desired.

Figure 4:
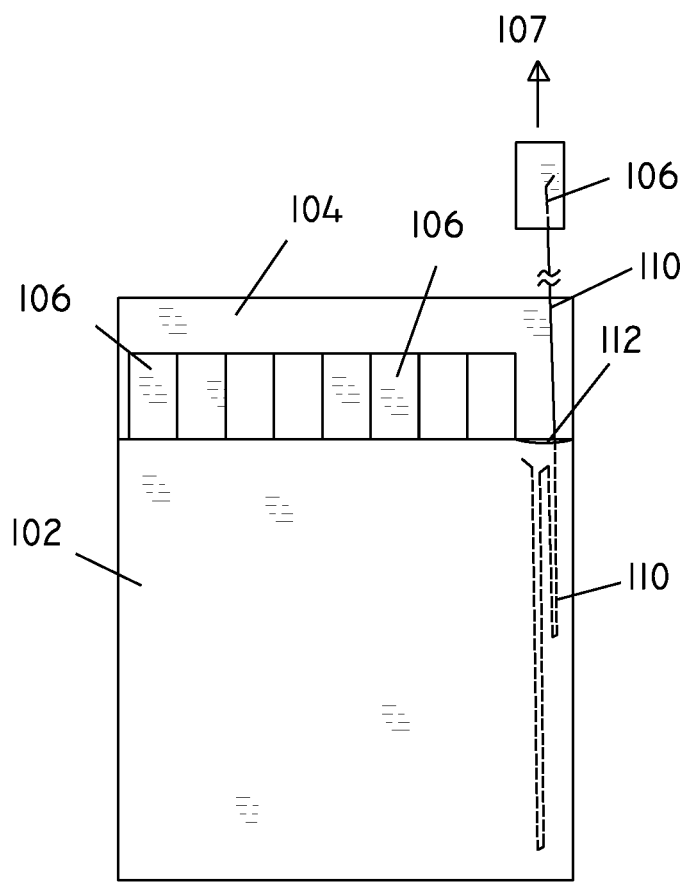
FIG. 4 is a front view of the dispensing system as an individual portion of floss is removed.

FIG. 4 is a float view of the dispensing system 100 as an individual portion of floss 110 is removed. To remove an individual portion of floss 110, the pull tab 106 is separated from the upper sheet 102 and/or the lower sheet 104. Accordingly, a portion of floss 110 that is attached to the corresponding pull cover 106 may be pulled from a cavity 108 of the dispensing system 100.

Figure 5:
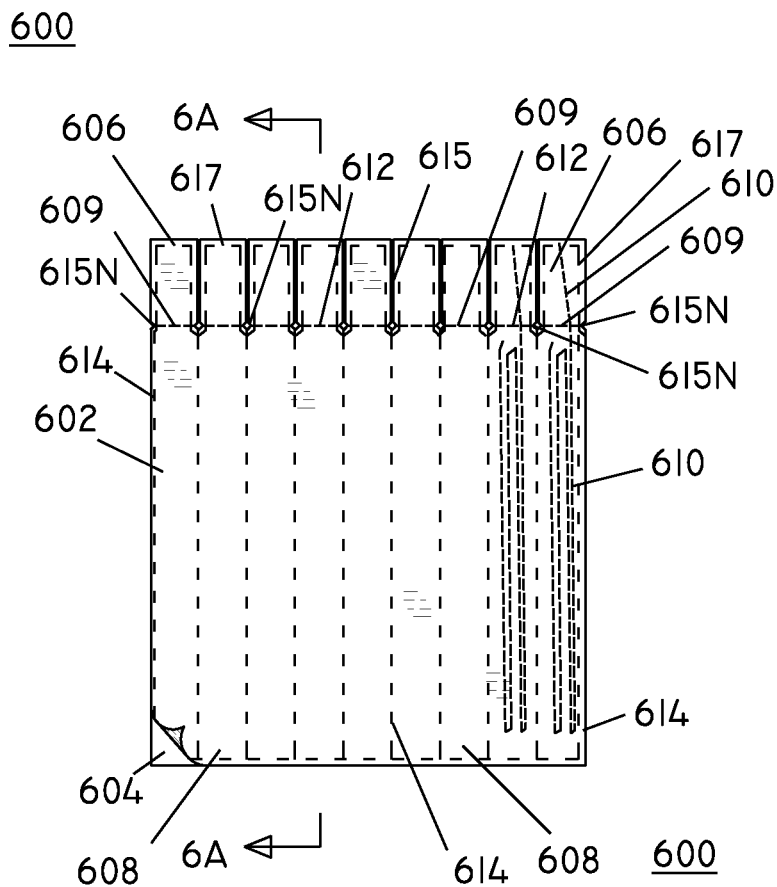
FIG. 5 is a front view of a dispensing system according to another embodiment of the present system.

FIG. 5 is a front view of a dispensing system 600 according to another embodiment of the present system. The dispensing system 600 may include one or more of an upper sheet 602, a lower sheet 604, a plurality of pull tabs 606, a plurality of cavities 608, and a plurality of floss portions 610.

The upper and lower sheets 602 and 604, respectively, form at least part of portions of the plurality of cavities 608. Each of the plurality of cavities 608 is preferably separate from adjacent cavities of the plurality of cavities 608, and may include an opening 612 through which one or more of the floss portions 610 may pass when a pull tab 606 is removed from the upper and/or lower sheets 602 and 604. respectively. Each of the pull tabs 606 may be separated from an adjacent pull tab 606 by separation such as a cutout 615 or weakened area such as, for example, a perforated area, a kiss cut area, etc, which may define an end portion of a corresponding pull tab 606. Further, each pull tab 606 may be attached to the upper sheet 602 and/or the lower sheet 604 at attachment areas 609 at which a corresponding pull tab 606 may separate from the upper sheet 602 and/or the lower sheet 604. One or more force focusing members such as, notches 615N (or cutouts, etc.) may be provided to increase a force on the weakened area 609 when the dispenser is opened. The opening 612 (e.g., see, FIG. 68) may be defined by weakened areas 609.

It is also envisioned that the weakened areas may also be formed by concentrating a force on a particular area and/or by orienting fibers in a desired fashion to cause a tear to progress along a desired path when subject to a force.

Figure 6A:
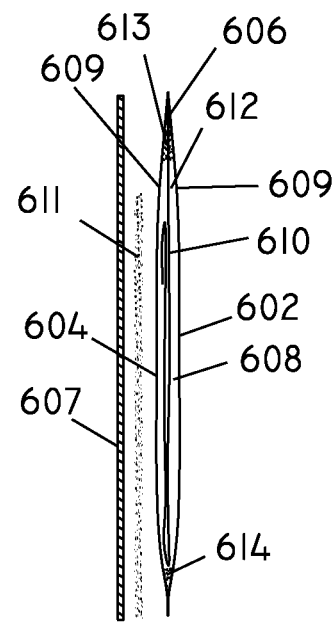
FIG. 6A is a cutaway side view of the dispensing system taken along lines 6-6 of FIG. 5.

FIG. 6A is a cutaway side view of the dispensing system 600 taken along lines 6-6 of FIG. 5. An individual portion of the floss 610 is situated in the cavity 608 and may be attached to the pull cover 606 using any suitable method. For example, an adhesive 613, heat bonding, etc., may be used to attach the floss 610 to the pull cover 606. The pull cover 606 may also include adhesive and/or cohesive layers such that one or more layers which form exterior portions of the pull cover 606 may be bonded to each other and/or form a seal (e.g., 617) around an outer periphery of the pull cover 606. Moreover, the pull cover 606 may also form at least part of and/or seal, at least part of the cavity 608. However, it is also envisioned that the cavity 608 may be sealed at the opening 612 using a seal which may include the corresponding portion of floss 610.

A backing (e.g., a rigid or semi-rigid backing, etc.) 607 to increase the rigidity of the upper and/or lower sheets 602 and 604, respectively, may be attached to a portion of lower sheet 604 using any suitable attachment method. For example, the attachment method may include, for example, an adhesive 611 situated between the backing 607 and the lower sheet 604. In operation, the pull tabs 606 may be pulled away from the backing 607. It is also envisioned a backing may be attached to the upper sheet 602, if desired.

Figure 6B:
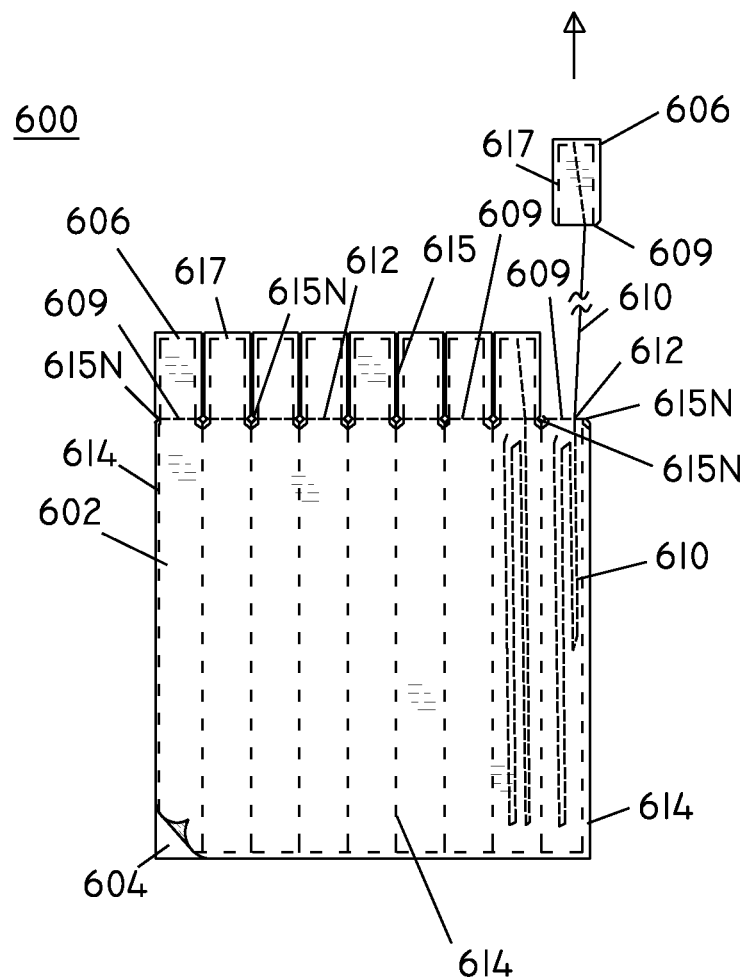
FIG. 6B is a front view of a dispensing system as it is opened.

FIG. 6B is a front view of a dispensing system 600 as it is opened. A pull tab 606 has been separated from the upper and/or lower sheets 102 and 104, respectively, at weakened area 609. A floss portion 610 is being pulled from a corresponding cavity 608. A restraining member (e.g., an adhesive, a friction enhancing portion, etc.) may restrain the floss such that the floss may be removed from the corresponding cavity 608 without undue bunching or knotting. The pull cover 606 may be twisted to aid in separation from either or both of the upper sheet 602 and the lower sheet 604.

Figure 7:
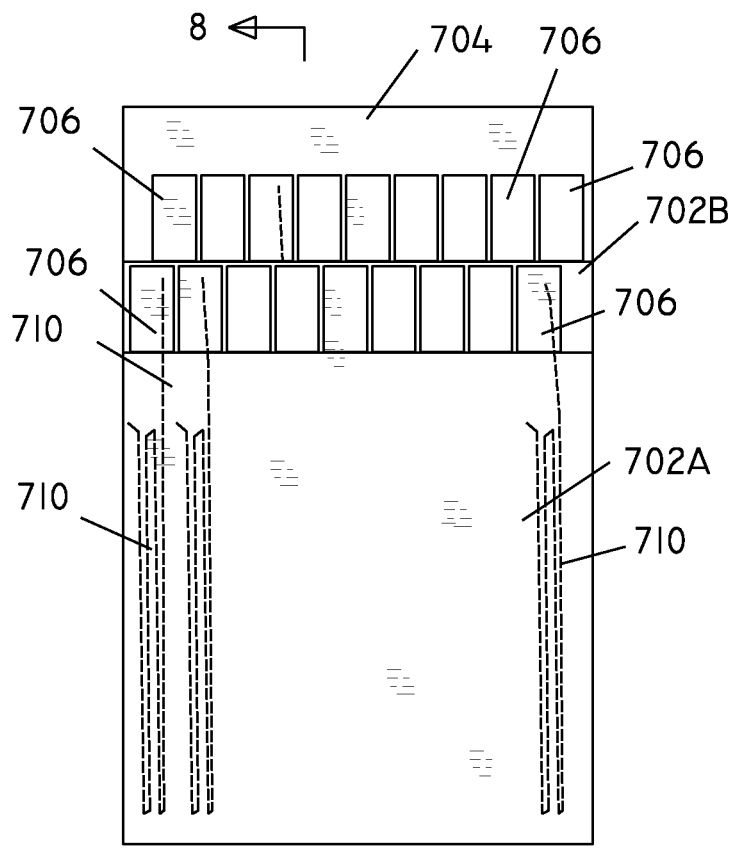
FIG. 7 is a front view of a dispensing system according to a further embodiment of the present system.

FIG. 7 is a front view of a dispensing system 700 according to a further embodiment of the present system. The dispensing system 700 may include layering of dispensers. For example, multiple layers of upper sheets and/or lower sheets may be used. Thus, the upper sheet may include a plurality of upper sheets 702A, 702B, etc, which may also function as a lower sheet (e.g., see, 702B) which is shared between layers (e.g., see, FIG. 8). This may save material and allow dense packaging. Further exterior portions of pull tabs 706 may overlap one or more adjacent pull tabs such that a user may easily grasp exposed portions of the pull tabs 706.

Figure 8:
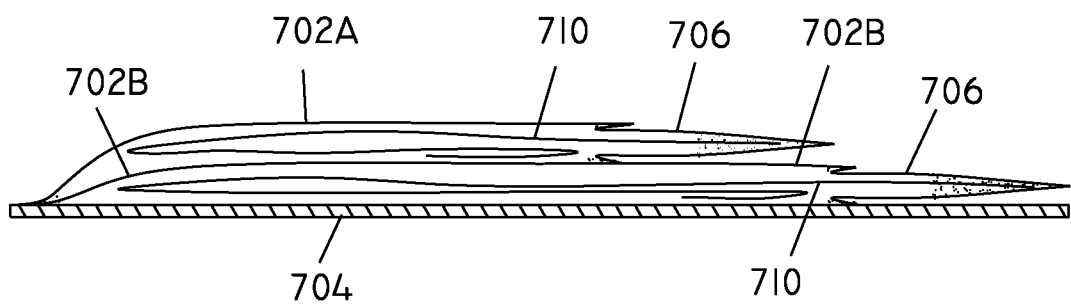
FIG. 8 is a cutaway side view of the dispensing system taken along lines 8-8 of FIG. 7.

FIG. 8 is a cutaway side view of the dispensing system 700 taken along lines 8-8 of FIG. 7. A lower sheet 704 may provide a desired level of rigidity to the dispenser system 700. For example, in applications, where it is desired that the dispenser system 700 fold, the lower sheet 704 may he flexible. However, when rigidity is desired, the lower sheet 704 may include a rigid and/or semi-rigid layer.

Figure 9A:
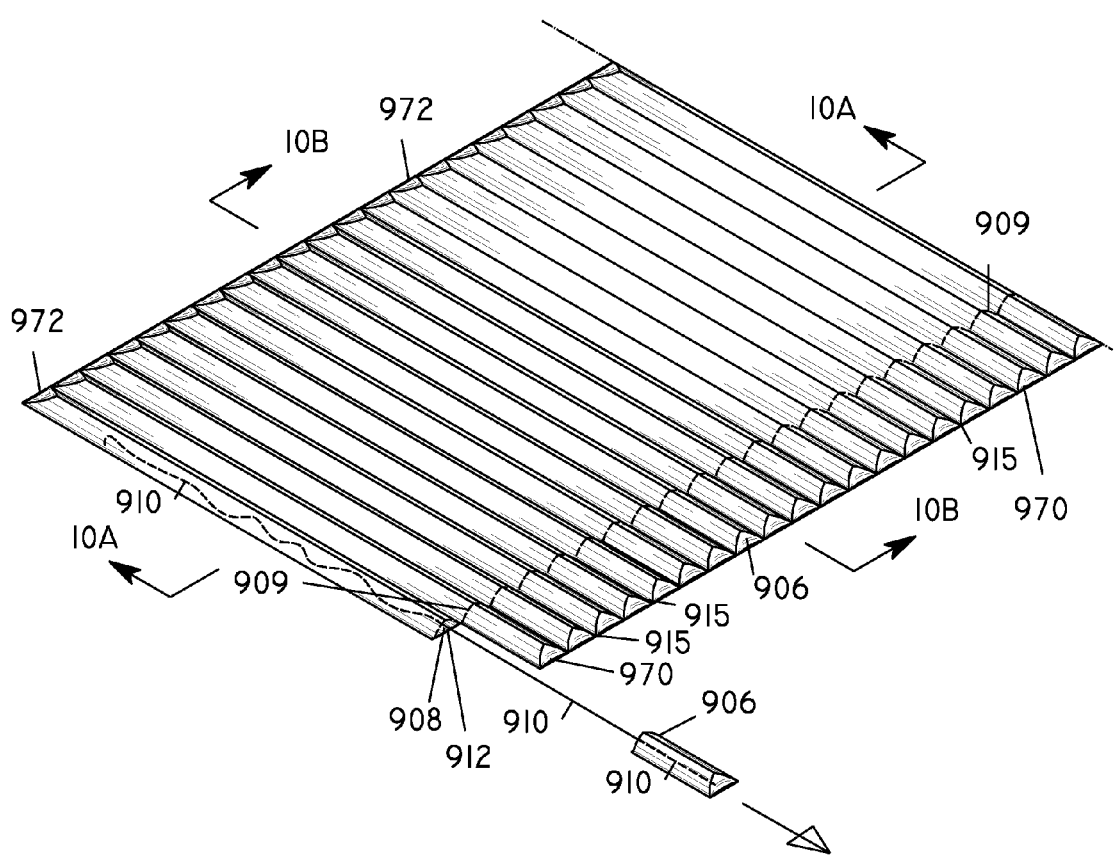
FIG. 9A is a perspective front view of a dispensing system according to yet a further embodiment of the present system.

FIG. 9A is a perspective front view of a dispensing system 900 according to yet a further embodiment of the present system. The dispensing system 900 may include one or more of an upper sheet 902, a lower sheet 904, a plurality of pull tabs 906, a plurality of cavities 908, and a plurality of floss portions 910.

The upper and lower sheets 902 and 904, respectively, form at least part of portions of the plurality of cavities 908. Each of the plurality of cavities 908 is preferably separate from adjacent cavities of the plurality of cavities 908, and may include an opening 912 through which one or more of the floss portions 910 may pass when a pull tab 906 is removed from the upper and/or lower sheets 902 and 904, respectively.

The upper and lower sheets 902 and 904, respectively, may be attached to each other to form one or more cavities 908 of the plurality of cavities 908 using any suitable method. Pull covers 906 may be separated from each other by a cutout portion 915 and/or a weakened area. The pull covers 906 may be formed integrally with the upper sheet 902 and/or the lower sheet 904 and may form a part of one or more of the cavities 908. End portions 970 and 972 may be sealed so as to define ends of each cavity 908 which lies therebetween. The upper sheet 902 and/or the lower sheet 904 may be formed from, a corrugated material so as to define the cavities between corrugated portions. A floss portion 910 may be located in each of the cavities 908 and may be attached to a corresponding pull tab 906. A weakened area 909 may define area at which a pull tab 906 may separate from the upper sheet 902 and/or the lower sheet 904 when the pull, tab 909 is pulled to open a corresponding cavity 908 and remove a portion of floss 910. Although the pull tab is formed integrally with the upper sheet 902 and/or the lower sheet 904, it is also envisioned that the pull tab may be formed separately from the upper sheet and/or the lower sheet.

Figure 9B:
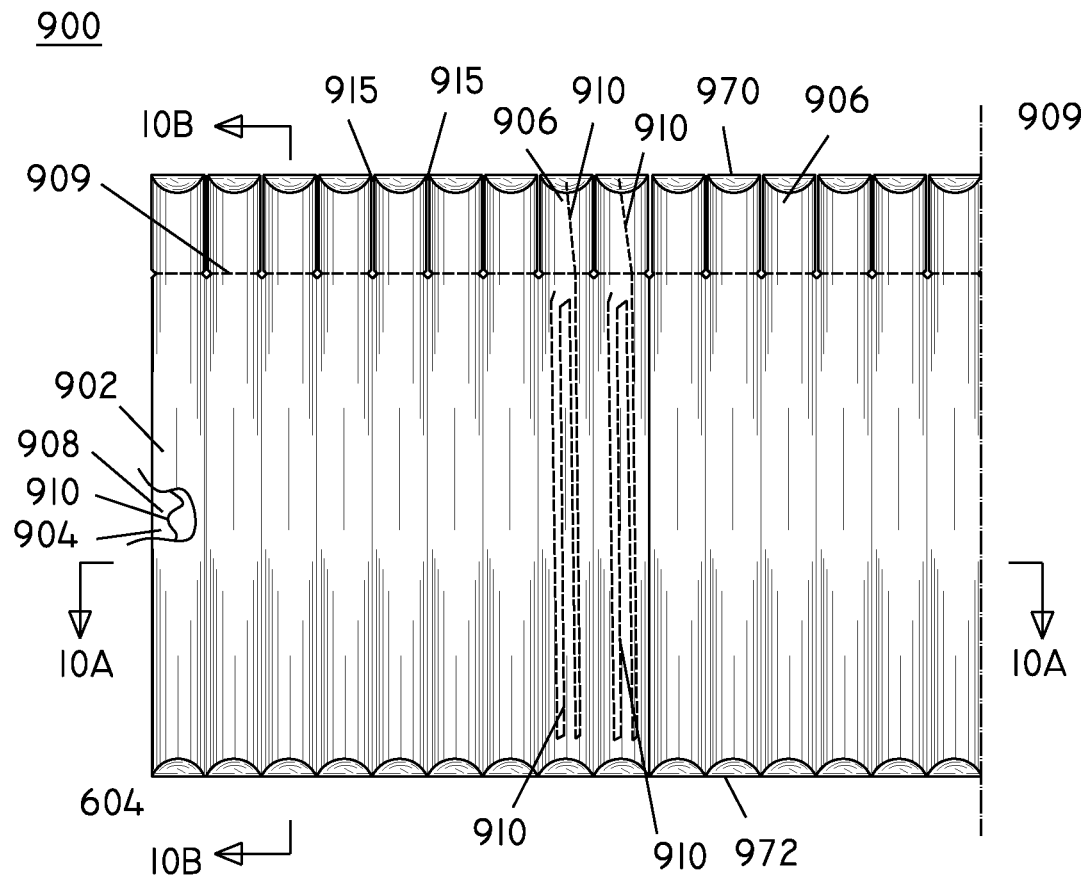
FIG. 9B is a front view of a dispensing system shown in FIG. 9A.

FIG. 9B is a front view of a dispensing system 900 shown in FIG. 9A.

Figure 10A:
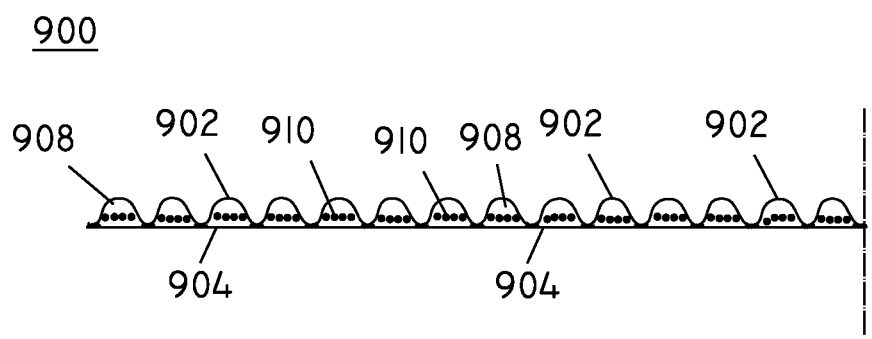
FIG. 10A is a cutaway view of the dispensing system taken along lines 10A-10A of FIG. 9B.

FIG. 10A is a cutaway view of the dispensing system 900 taken along lines 10A-10A of FIG. 9B. The upper sheet 902 may include pleats (or flutes) and may be attached to the lower sheet 904 using any suitable method (e.g., adhesives, bonding, etc.).

Figure 10B:
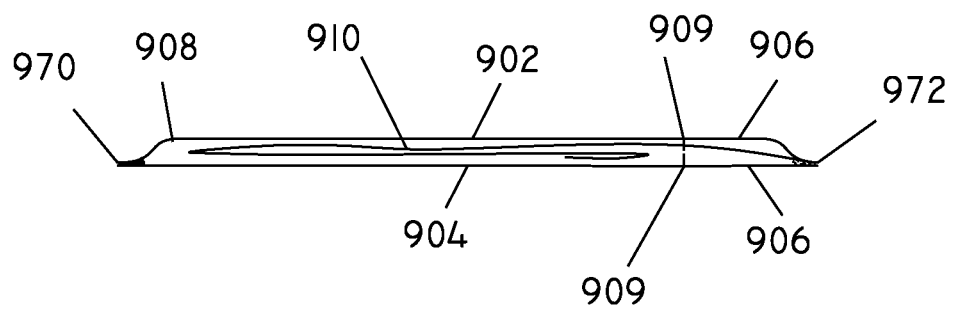
FIG. 10B is a cutaway view of the dispensing system taken along lines 10B-10B of FIG. 9B.

FIG. 10B is a cutaway view of the dispensing system 900 taken along lines 10B-10B of FIG. 9B.

Figure 10C:
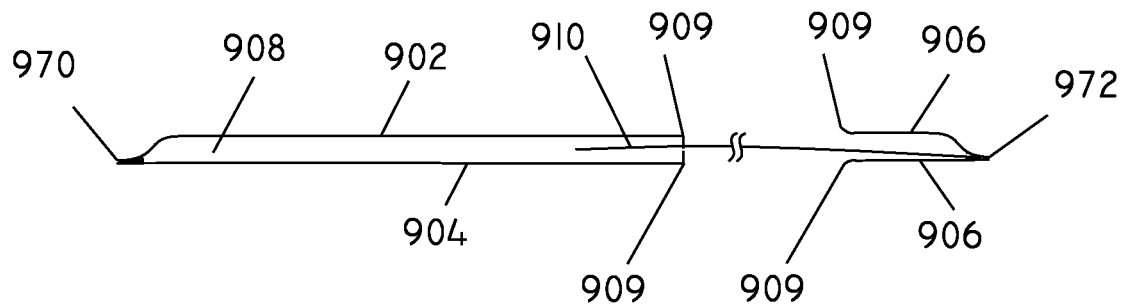
FIG. 10C is a cutaway view of the dispensing system of FIGS. 9A-10B shown in the process of removing a floss portion.

FIG. 10C is a cutaway view of the dispensing system 900 of FIGS. 9A-10B shown in the process of removing a floss portion 910. The pull tab 906 separates from the upper and/or lower sheets 902 and 904, respectively, the weakened area 909. A portion of floss 910 that is located in a corresponding cavity 908 may be removed from the cavity via an opening 912. The weakened area 909 may include an area which is physically weakened, (e.g., by scoring, etc.) or may be an area in which forces concentrate so as to cause separation when the pull tab 906 is pulled to dispense a portion of floss 910. Accordingly, cutouts, notches, etc. may be provided to concentrate forces, if desired so that separation may occur at desired areas.

Figure 11A:
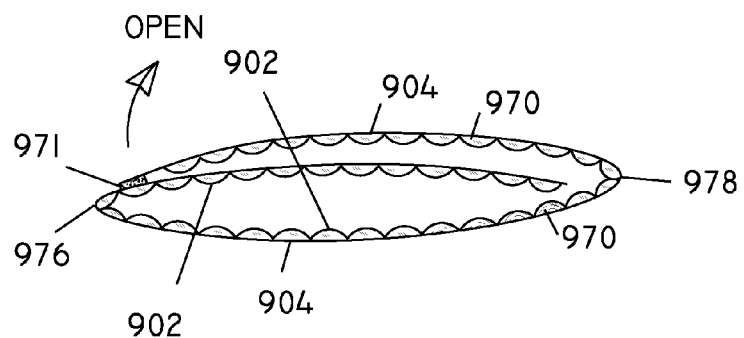
FIG. 11A is a top view illustration of a dispensing system according to another embodiment of the present system.

FIG. 11A is a top view illustration of a dispensing system 1100 according to another embodiment of the present system. The dispensing system 1100 be formed from a dispenser such as, for example, dispenser 900 and may be of sufficient length such that it may be curled and/or folded over itself (e.g., at folds 976. 978). A locking method such as a pressure-sensitive-adhesive (PSA) layer, etc. may be used to hold the dispenser 900 in a folded position.

Figure 11B:
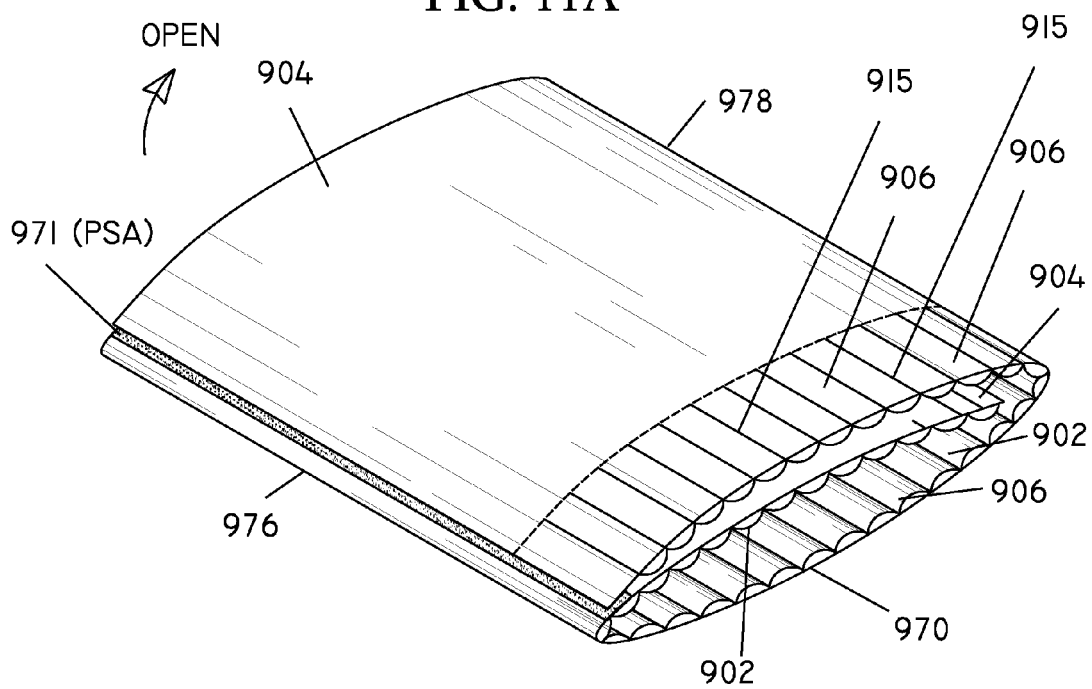
FIG. 11B is a perspective view illustration of the dispensing system, shown in FIG. 11A.

FIG. 11B is a perspective view illustration of the dispensing system shown in. FIG. 11A.

Figure 12A:
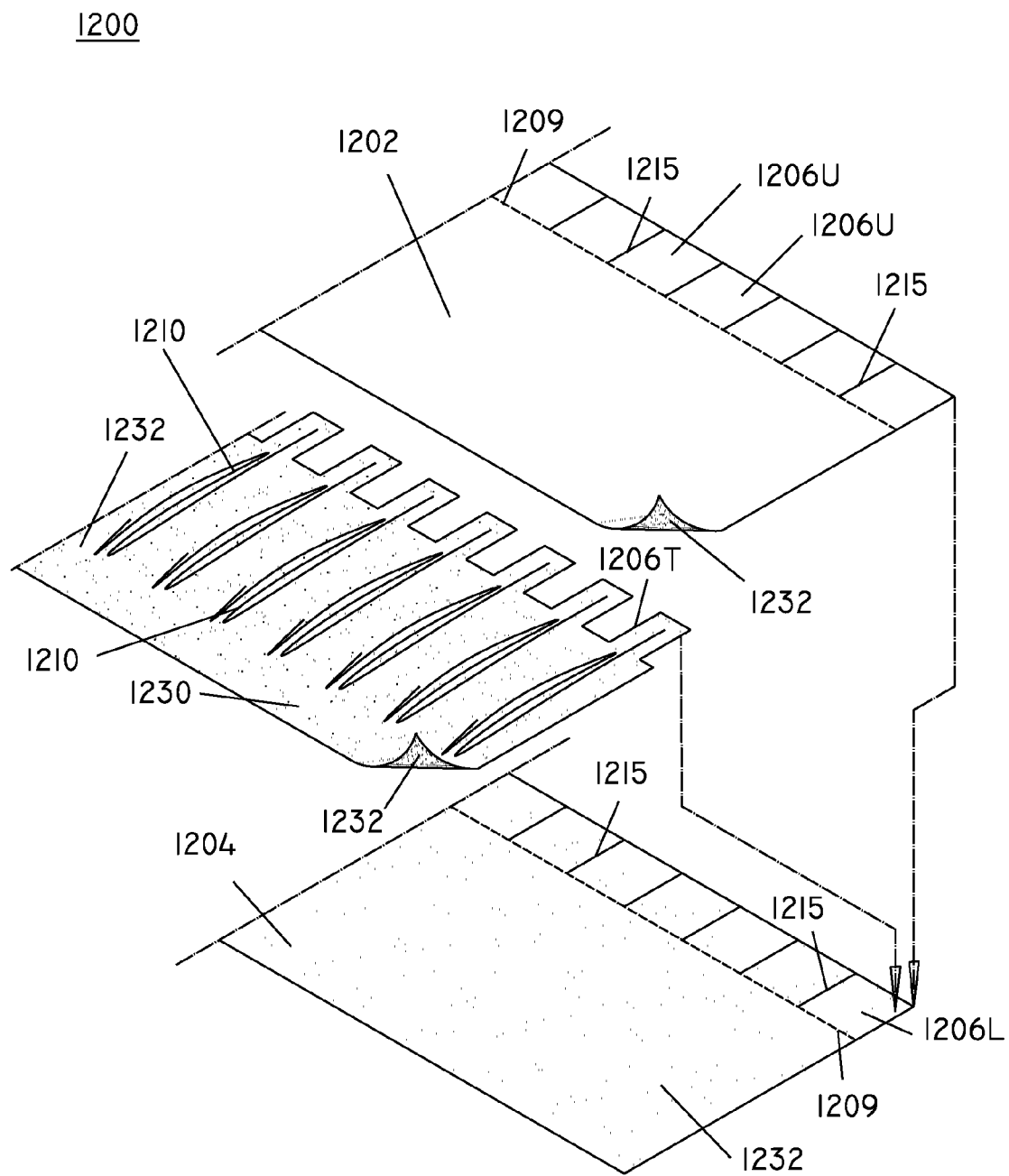
FIG. 12A is an exploded perspective view of a dispensing system according to yet another embodiment of the present system.

FIG. 12A is an exploded perspective view of a dispensing system 1200 according to yet another embodiment of the present system. The dispensing system 1200 may Include one or more of an upper sheet 1202, a lower sheet 1204, a plurality of pull tabs, a plurality of cavities, and a plurality of floss portions 1210.

The upper and lower sheets 1202 and 1204, respectively, form at least part of portions of the plurality of cavities. The upper and lower sheets 1202 and 1204, respectively, may be attached to each other to form one or more cavities of the plurality of cavities using any suitable method. Pull covers may include portions 1206U, 1206L and/or 1206T and may be separated from each other by cutout portions 1215 and/or a weakened area 1209. The pull covers may be formed integrally with the upper sheet 1202 and/or the lower sheet 1204 and may form a part, of one or more of the cavities. An adhesive such as, for example, a cohesive 1232 may be deposited on adjacent major surfaces of the upper sheet 1202, and/or the lower sheet 1204.

The floss portions 1210 may be mounted upon a carrier 1230 which may be situated between the upper sheet 1202 and/or the lower sheet 1204. The cohesive 1232 may also coat upper and lower major surfaces of the carrier 1230. The carrier may include tab portions 1206T which may form at least part of corresponding pull tabs 1206. End portions of the floss portions 1210 may be attached to the tab portions 1206T using any suitable method. Attachment members may be used to locate the floss portions 1210 relative to the carrier 1230. The attachment members may include adhesives, tabs, etc. Moreover, the floss portions 1210 may be threaded into the carrier 1230 and may pull free when a corresponding floss portion is removed from a corresponding cavity of the dispensing system 1200. This is illustrated in FIG. 12C which illustrates an exploded side view illustration of a floss portion 1210 threaded through a carrier 1230C of a dispensing system 1200C.

Figure 12B:
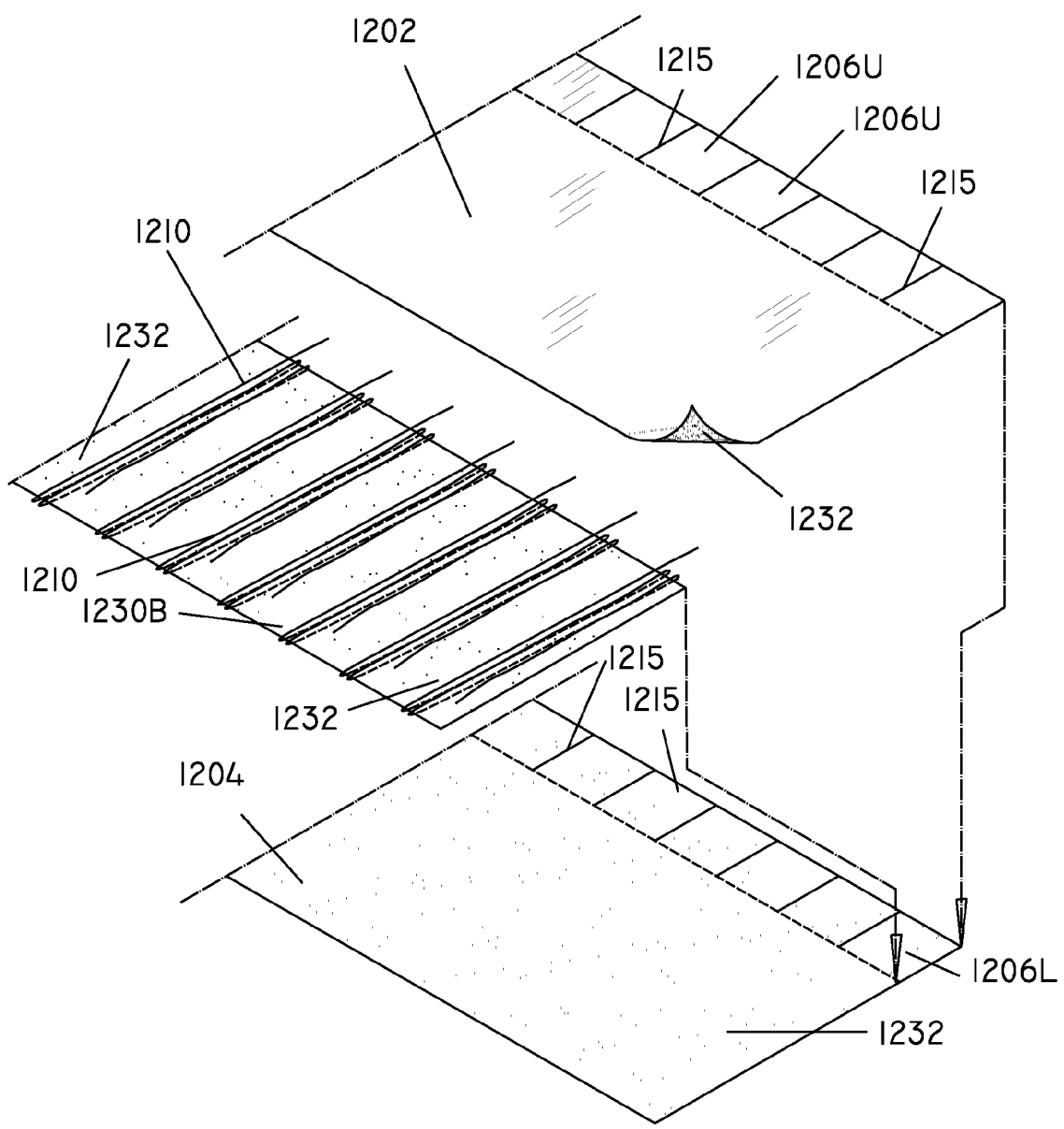
FIG. 12B is an exploded perspective view of a dispensing system according to yet another embodiment of the present system.
Figure 12C:
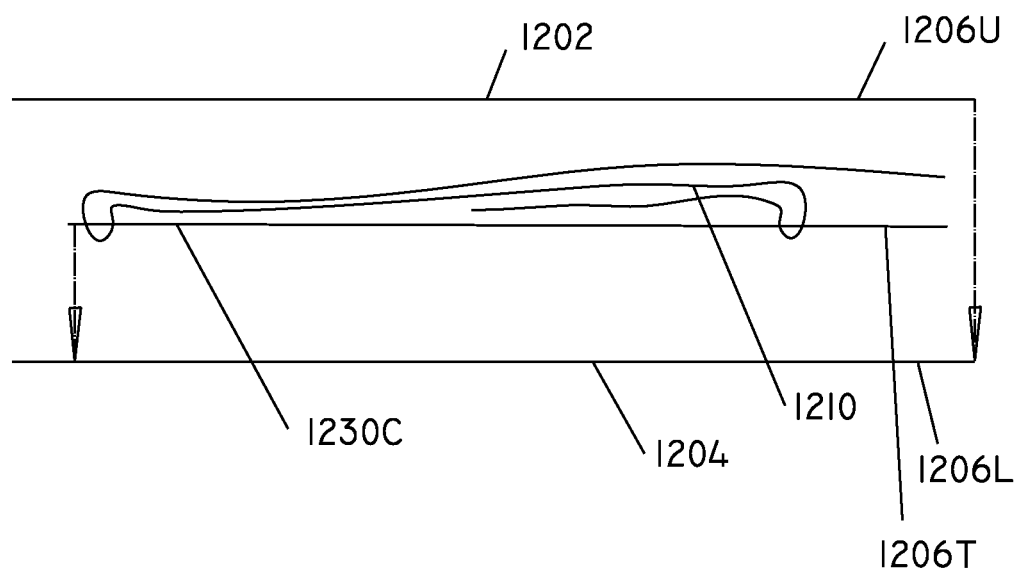
FIG. 12C which illustrates an exploded side view illustration of a floss portion threaded through a carrier.

FIG. 12B is an exploded perspective view of a dispensing system 1200B according to yet another embodiment of the present system. The dispensing system 1200B is similar to the dispensing system 1200, however, carrier 1200B includes portions of floss 1210 which wrap around the carrier 1200B. Accordingly, a portion of floss 1210 may rip through the carrier 1230 when it is removed from a corresponding cavity. The carrier 1230B may be formed from a material may rip easily so as to allow the portion of floss 1210 to be separated from the carrier 1230B.

FIGS. 13A-13E are cutaway views of pull tabs of dispensing systems according to various embodiments of the present system. For example, with reference to FIG. 13A, a poll tab 1306A may be formed integrally with an upper sheet 1302 and may be attached to the lower sheet using any suitable method such as, for example, an adhesive 1397A.

Figure 13A:
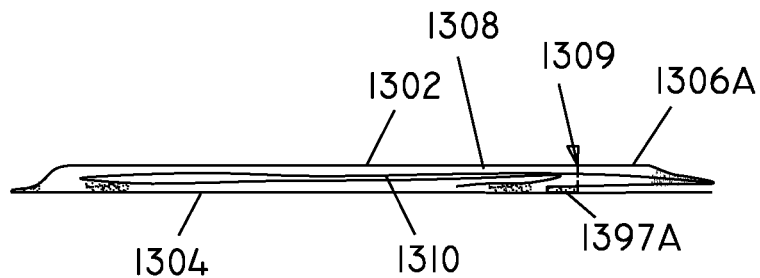
FIGS. 13A-13E are cutaway views of pull tabs of dispensing systems according to various embodiments of the present system.
Figure 13B:
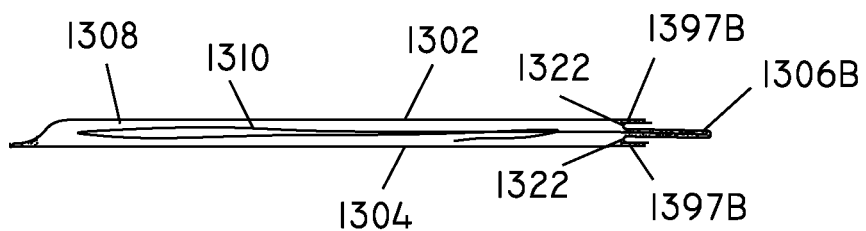

With reference to FIG. 13B, a pull tab 1306B may be attached to upper and lower sheets 1302 and 1304, respectively, using any suitable method such as, for example, an adhesive 1397B and may be situated adjacent to folds 1322 of the pull tab 1306B.

Figure 13C:
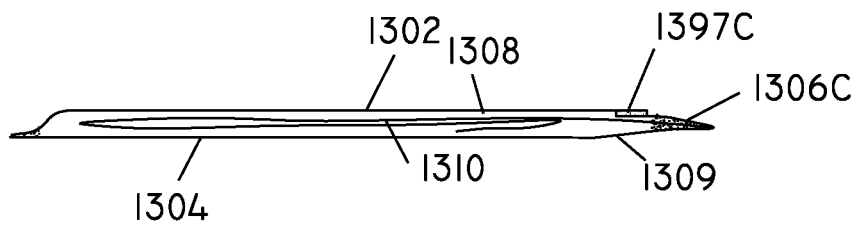

With reference to FIG. 13C, a pull tab 1306C may be formed integrally with a lower sheet 1304 and may be attached to an upper sheet 1302 using, any suitable method, such as, for example, an adhesive 1397C.

Figure 13D:
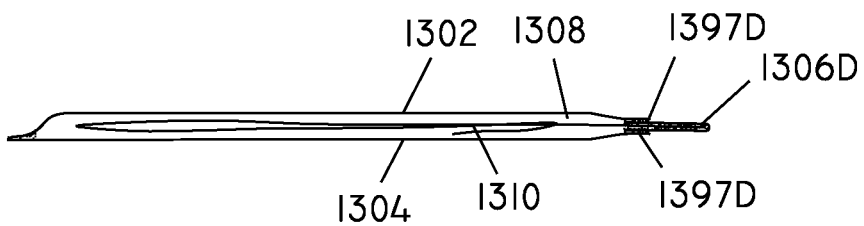

With reference to FIG. 13D, pull tab 1306D may be attached to upper and lower sheets 1302 and 1304, respectively, using any suitable method such as, for example, an adhesive 1397D.

Figure 13E:
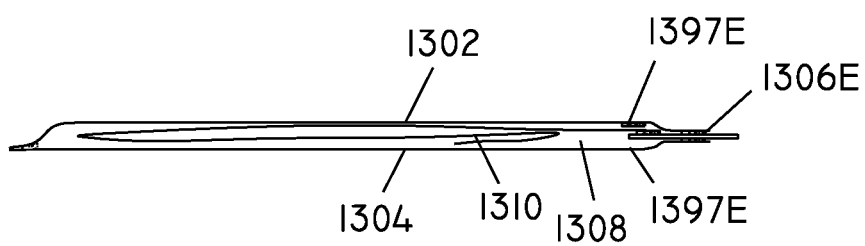

With reference to FIG. 13E, pull tab 1306E may be attached to upper and lower sheets 1302 and 1304, respectively, using any suitable method such as, for example, an adhesive 1397B. A portion of floss 1310 in a corresponding cavity 1308, may be attached to the pull tab 1306E using any suitable method.

Figure 14A:
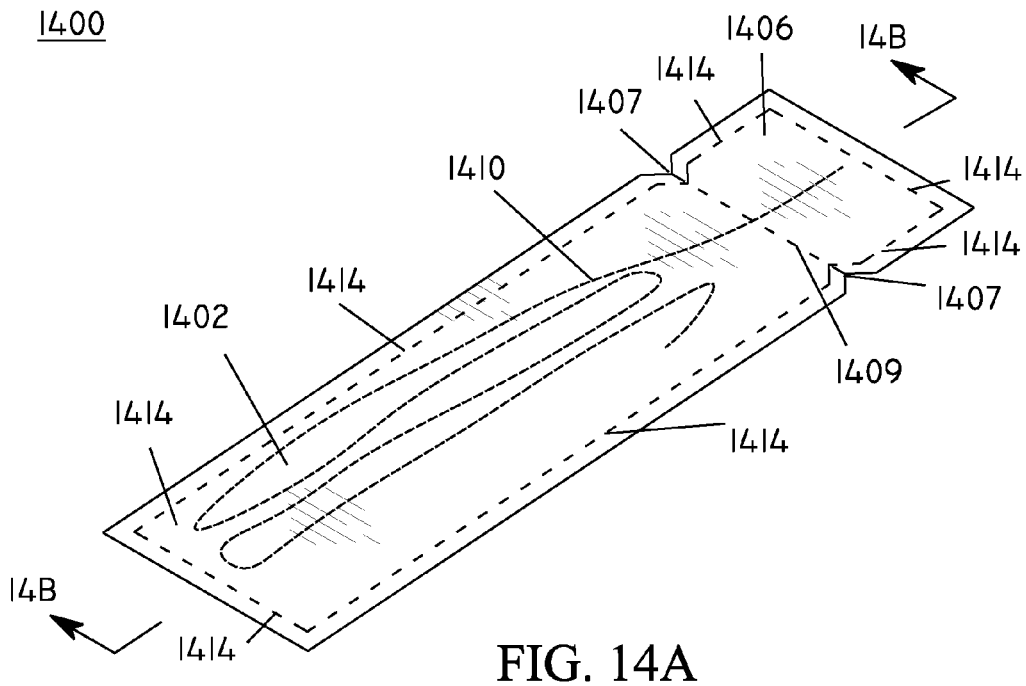
FIG. 14A is a perspective front view of a dispensing system according to an embodiment of the present system.

FIG. 14A is a perspective front view of a dispensing system 1400 according to an embodiment of the present system. The dispensing system 1400 may include one or more of a upper sheet 1402, a lower sheet 1404, a pull tab 1406, a cavity 1408, and a floss portion 1410.

The upper and lower sheets 1402 and 1404, may be attached to each other so as to form at least part of the cavity 1408 which may hold the floss portion 1410. For example, the upper sheet 1402 and the lower sheet 1404 may be attached to each other along an outer periphery as shown by line 1414 and/or line 1409. A weakened area 1409 may extend across a portion of the dispensing system 1410 and may be located between notches 1407 (cutouts, etc.) which may increase a separation force in the weakened area. However, it is also envisioned that the weakened area 1409 may be formed by scoring and/or by orienting fibers in a desired direction.

The pull tab 1406 may be defined by the weakened area 1409 on one side, such that the pull tab 1406 may separate from one or more of the upper sheet 1402 and the lower sheet 1404 when the dispensing system 1400 is opened.

Figure 14B:
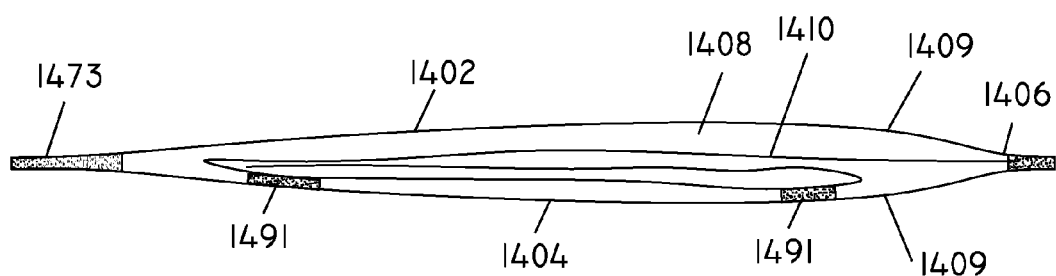
FIG. 14B is a cutaway side view of the dispensing system taken along lines 14B-14B of FIG. 14A.

FIG. 14B is a cutaway side view of the dispensing system 1400 taken, along lines 14B-14B of FIG. 14A. The floss portion 1410 is located in the cavity 1408 and is attached to the pull tab 1406. A second tab portion 1473, suitable for grasping by a user, may be provided. Accordingly, a user may grasp the second tab portion 1473 when opening the dispensing system 1400.

Figure 14C:
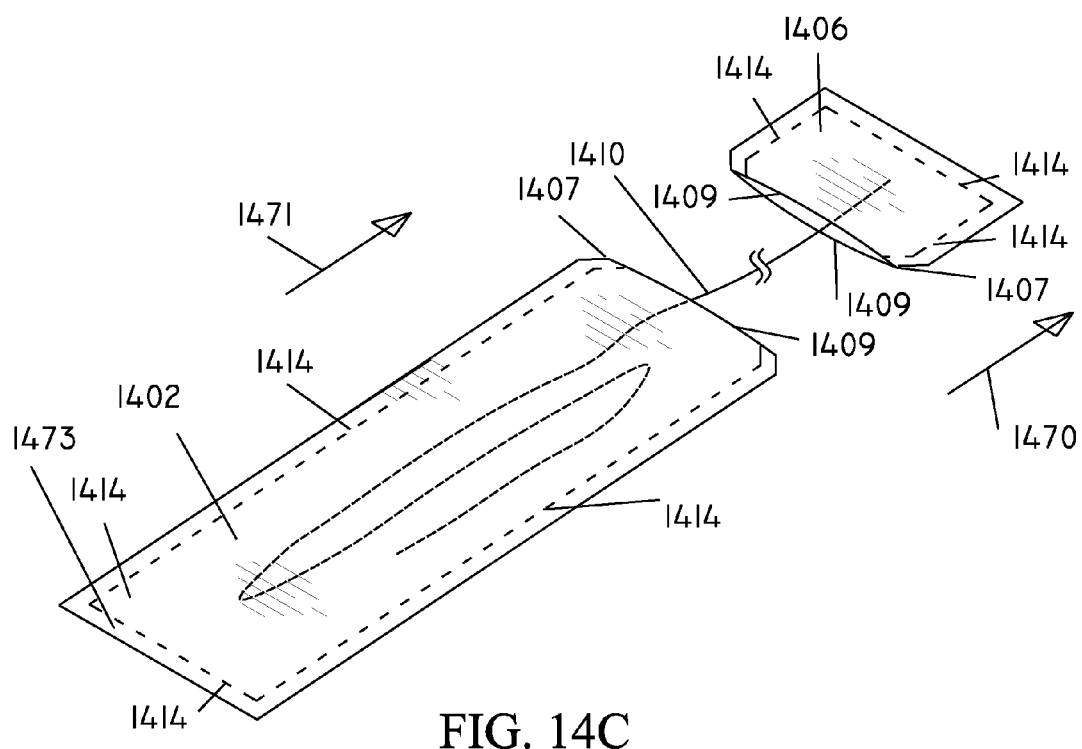
FIG. 14C is a perspective view of the dispensing system as an individual portion of floss is removed.

FIG. 14C is a perspective view of the dispensing system 1400 as an individual portion of floss 1410 is removed. To remove an individual portion of floss 1410, the pull tab 1406 is separated from the upper sheet 1402 and/or the lower sheet 1404. When pulling in a direction of arrow 1470, the pull tab 1406 may separate from the upper sheet 1402 and/or the lower sheet 1404 at the weakened area 1409. Accordingly, a portion of floss 1410 that is attached to the corresponding pull tab 1406 may be pulled from the cavity 1408 in of the dispensing system. 1400. The floss portion 1410 may be pulled from the cavity via the opening 1412 and may be partially or fully removed from the cavity 1408. A friction member such as, for example, an adhesive 1491, a carrier, etc., may be used to increase a force required to remove the floss portion 1410. Further, this force may increase a tension on the floss and prevent, bunching and/or knotting during removal. The floss portion 1410 may unwind as illustrate by arrow 1471. However, it is also envisioned that tire floss may unwind in a direction which is longitudinal and/or transverse to an axis (e.g., a longitudinal and/or transverse axis) of the dispensing pack 1400.

Figure 14D:
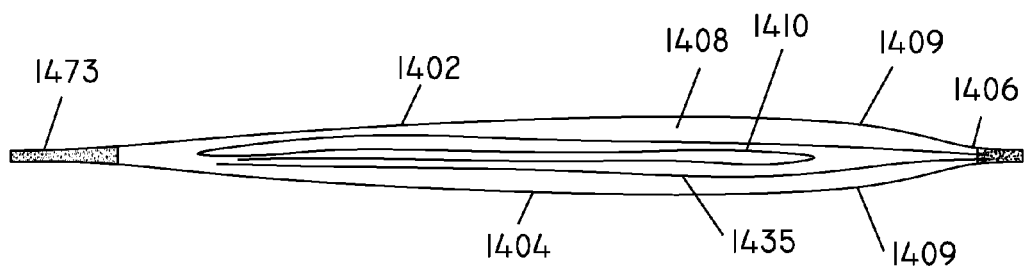
FIG. 14D is a cutaway side view of an alternative embodiment of the dispensing system taken along lines 14B-14B of FIG. 14A.

FIG. 14D is a cutaway side view of an alternative embodiment of the dispensing system 1400D taken along lines 14B-14B of FIG. 14A. Dispensing system 1400D is similar to the dispensing system 1400, however, a strip 1435 such as, for example, breath strip (e.g., a LISTERINE™ POCKET-PAKS™ Breath Strip) may be located in the cavity 1408. The strip 1435 may be attached to the pull tab 1406 and may be removed from the cavity 1408 by via the opening 1412 when the poll tab 1406 is removed from the upper sheet 1402 and/or the lower sheet 1404.

Figure 14E:
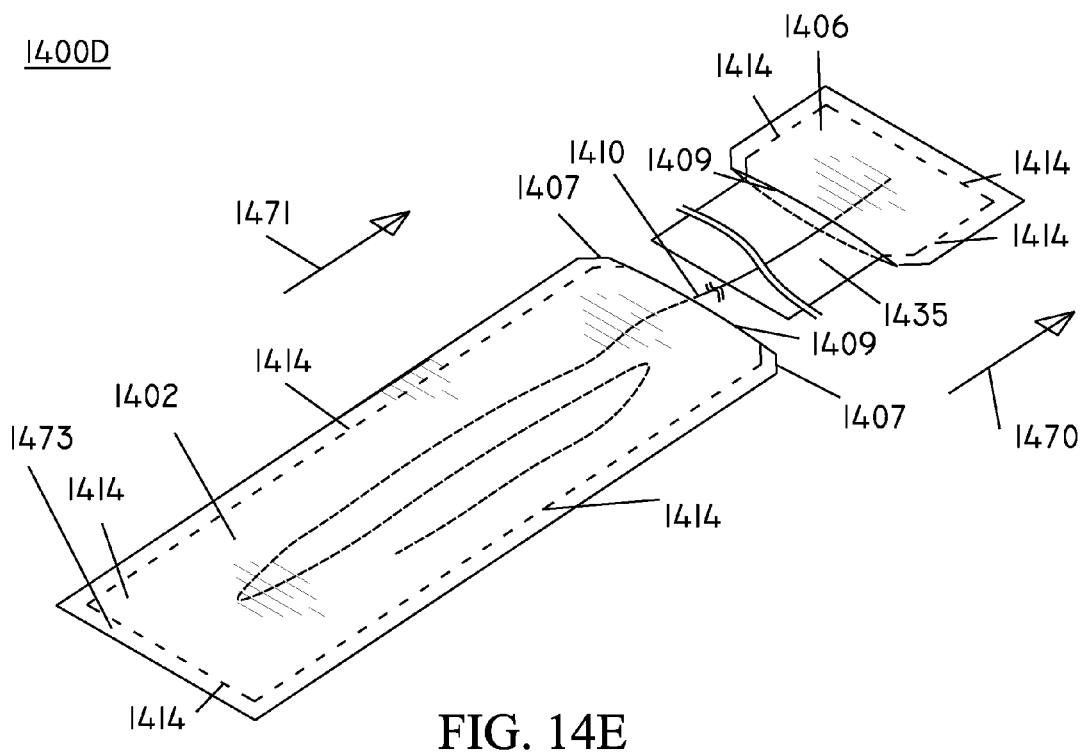
FIG. 14E is a perspective view of the dispensing system of FIG. 14D as an individual portion of floss is removed.

FIG. 14E is a perspective view of the dispensing system 1400D as an individual portion of floss 1410 is removed. The strip 1435 may be torn away from the pull tab 1406, if desired.

Figure 15A:
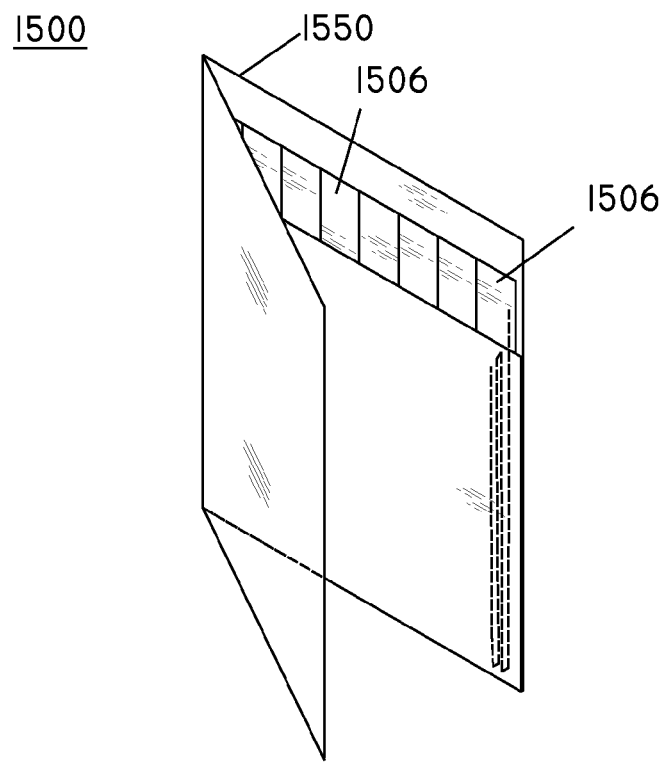
FIGS. 15A, 15B, 16, and 17 are perspective views of dispensing systems including dispensing packs according to yet other embodiments of the present system.

FIGS. 15A. 15B, 16 and 17 are perspective views of dispending systems including dispensing packs according to yet other embodiments of the present system. For the sake of clarity, the dispending packs shown and described in FIGS. 1 through 14D may be referred to as dispensers and may be arranged in various combinations to form dispending packs.

Figure 15B:
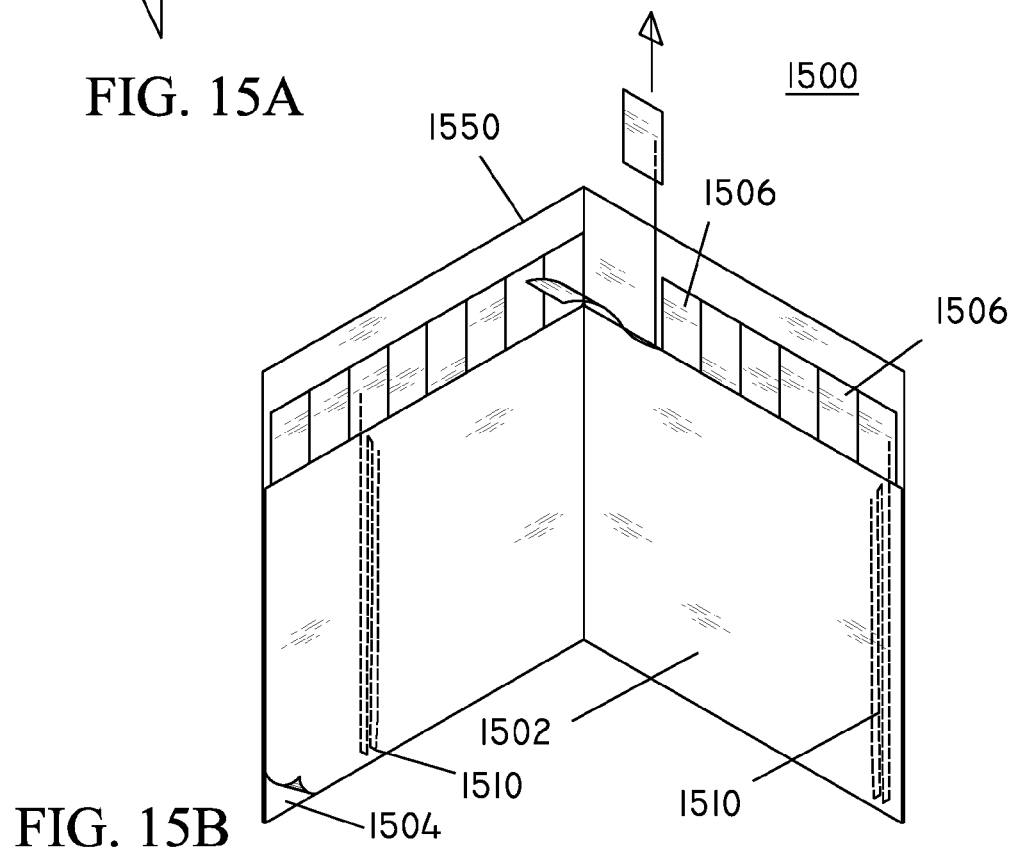

With reference to FIGS. 15A and 15B, a perspective view of a dispensing pack 1500 is shown including a folded outer covering 1550. Pull tabs 1506 of one or more dispensers may be accessed and separated from upper and/or lower sheets 1502 and 1504, respectively, to remove individual floss portions 1510. A locking member (e.g., a latch, a tab, an adhesive, a magnet, etc) may be used to hold the outer covering in a closed position.

Figure 16:
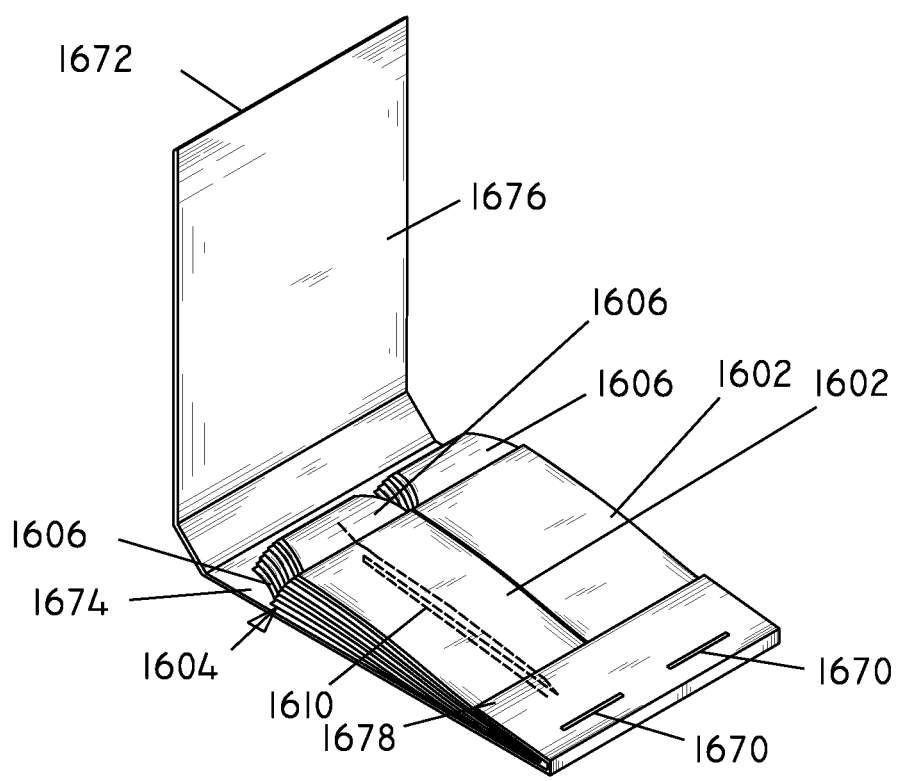

With reference to FIG. 16, a perspective view of matchbook-type dispensing pack 1600 is shown. The matchbook-type dispensing pack 1600 may include an outer covering 1672 which may include one or more of a back portion 1674, a lid portion 1676 and a closing portion 1678. A plurality of dispensers (e.g., dispending systems including an upper sheet 1602, a lower sheet 1604, a pull tab 1606, floss portions, etc.) may be attached to the outer covering using any suitable method such as, for example, holding members 1670 (e.g., adhesives, staples, etc.). In operation, a user may open the outer covering 1672 and separate a pull tab 1606 from the upper sheet 1602 and/or the lower sheet 1604, and remove a floss portion 1610 attached to the pull tab 1606. The pull tabs 1606 may also be arranged so that they are adjacent the closing portion 1678.

Figure 17:
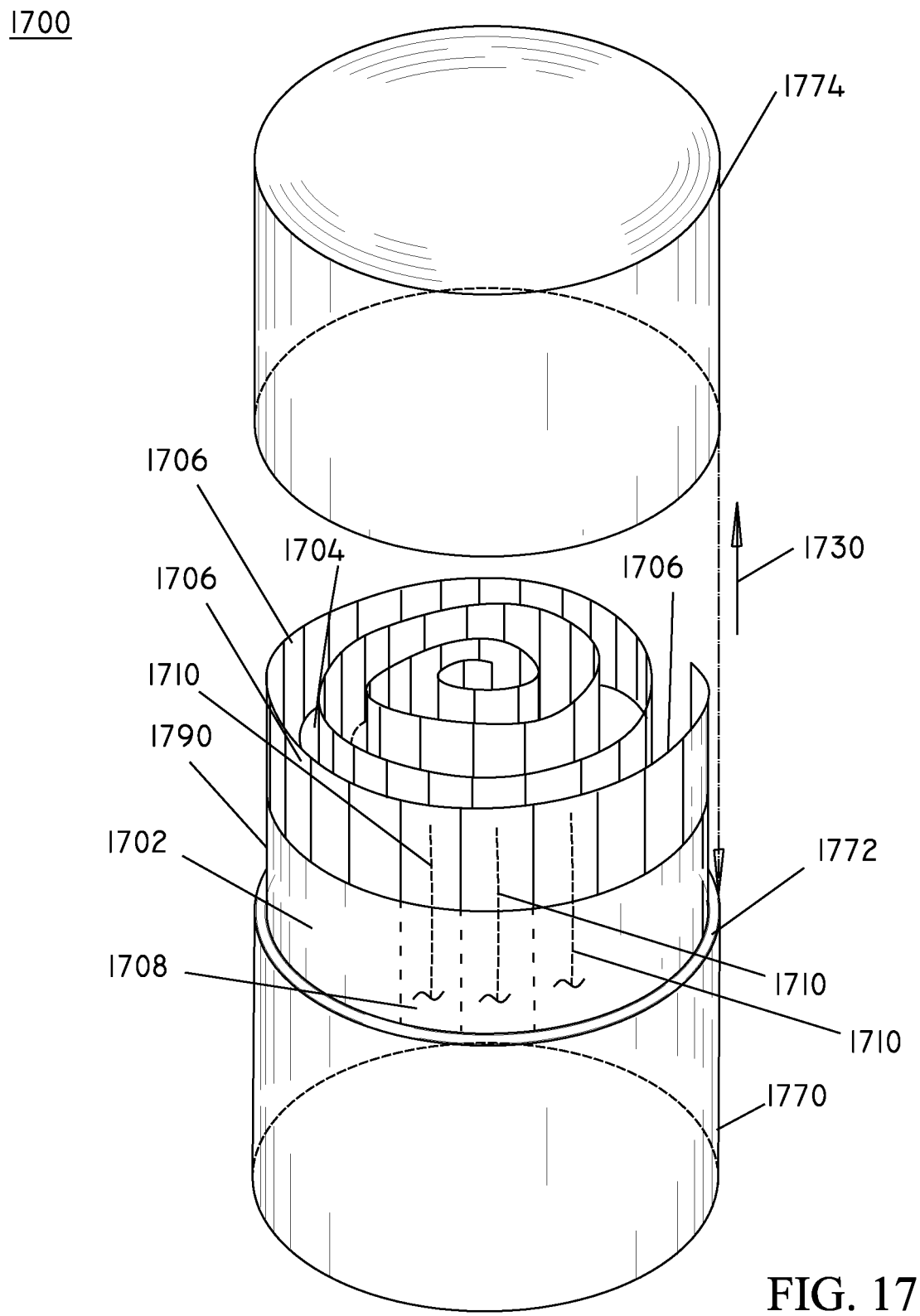
Figure 18:
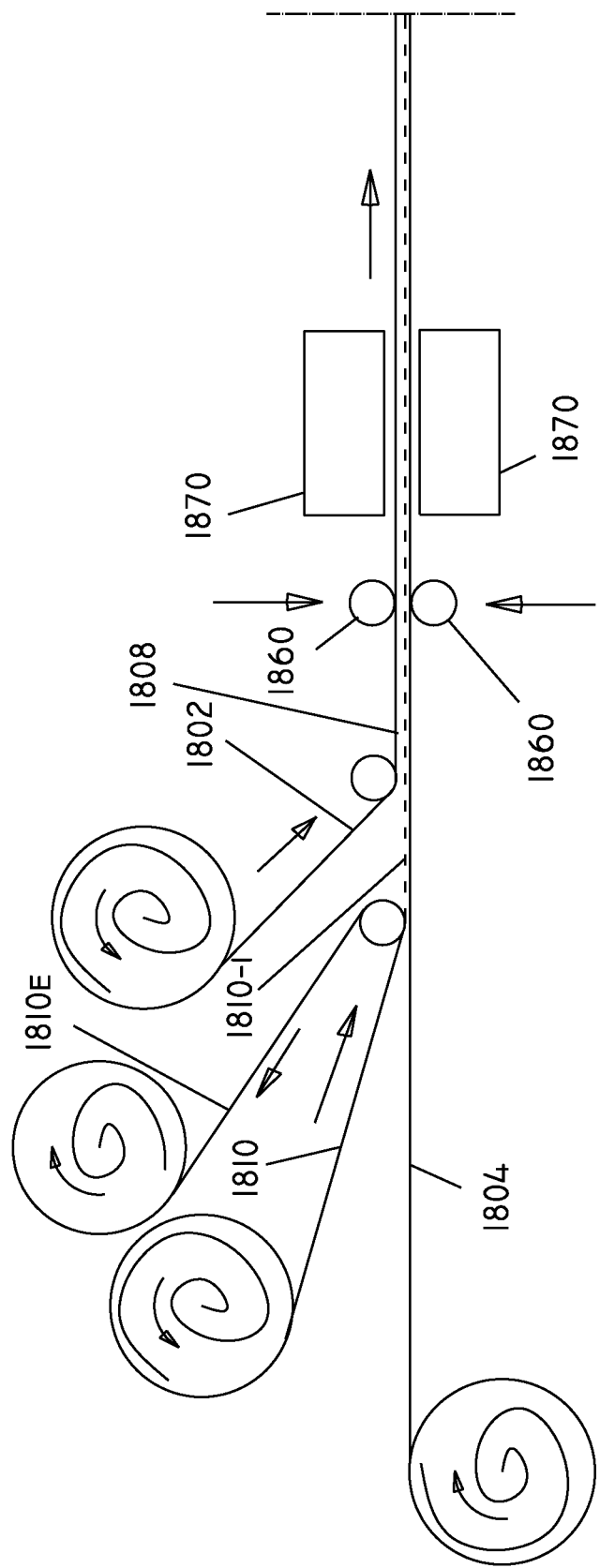
FIG. 18 is a process for forming dispensers according to an embodiment of the present system.

With reference to FIG. 17, an exploded perspective view of a roll-type dispensing pack 1700 is shown. The dispensing pack 1700 may include one or more of a base portion 1770, a cover portion 1774 and one or more dispensers 1790 situated in the base portion 1770. The base portion 1770 may include a flange such as flange 1772 which may limit the travel of the cover portion 1774 when in a closed position. The dispensers 1790 may be arranged in a rolled configuration such that pull tabs 1706 may be removed by pulling in a direction of arrow 1730 to remove an individual floss portion 1710 from a corresponding cavity 1708. An upper sheet 1702 may be attached to a lower sheet so as to form the cavities 1708. One or more of the upper sheet 1702 and/or the lower sheet 1704 may include a corrugated material as shown in FIGS. 9A through 11B.

Blocking members may be used to increase a thickness of the dispensing system and/or to reduce or prevent a users hand from applying pressure to a portion of floss as it is being removed via the opening.

Each of the floss portions may be folded, wrapped, or otherwise arranged so that a sufficient length of floss may be stored within a respective cavity. For example, according to an embodiment a length of a portion of floss may be greater than twelve inches. However, other lengths (e.g., shorter or longer) are also envisioned.

The floss portions may include conventional flosses and may be waxed, unwaxed, include a paste or other additives such as, for example, a mint, fluoride, other flavorings or coatings, breath fresheners, etc, Moreover, the floss may be formed from a material which has a positive and/or a negative poisson ratio. Further, the floss may include areas which have a negative poisson ratio and areas which include a positive poisson ratio. For example, in certain areas a cross section of floss may expand when subject to a. tension and in other areas a cross section of floss may contract when subject to a tension. Accordingly, a user may place sections of floss having a negative and/or a positive poisson ratio in desired areas to remove contaminants.

A process for forming dispensers according to an embodiment of the present system is shown in FIG. IS. The process may include placing individual portions of floss from floss webbing 1810 on webbing 1804 which may form a plurality lower sheets 1804. The floss webbing 1810 may include individual portions of floss 1810*i* and may include a backing 1810E and/or a carrier portion which may be removed from the individual portions of floss 1810*i*. The individual portions of floss 1810*i* may include a carrier. Webbing 1802 may then be placed over an adjacent side of the webbing 1804 to form cavities 1808 which include a corresponding individual portion of floss 1810*i*. Pressure rollers 1860 (or optional pressure plates) may seal the webbing 1802 to the webbing 1804 to each other. A die/kiss cutter 1870 may then perform a cutting operation to form pull tabs 1806 and/or separate packages.

Figure 19:
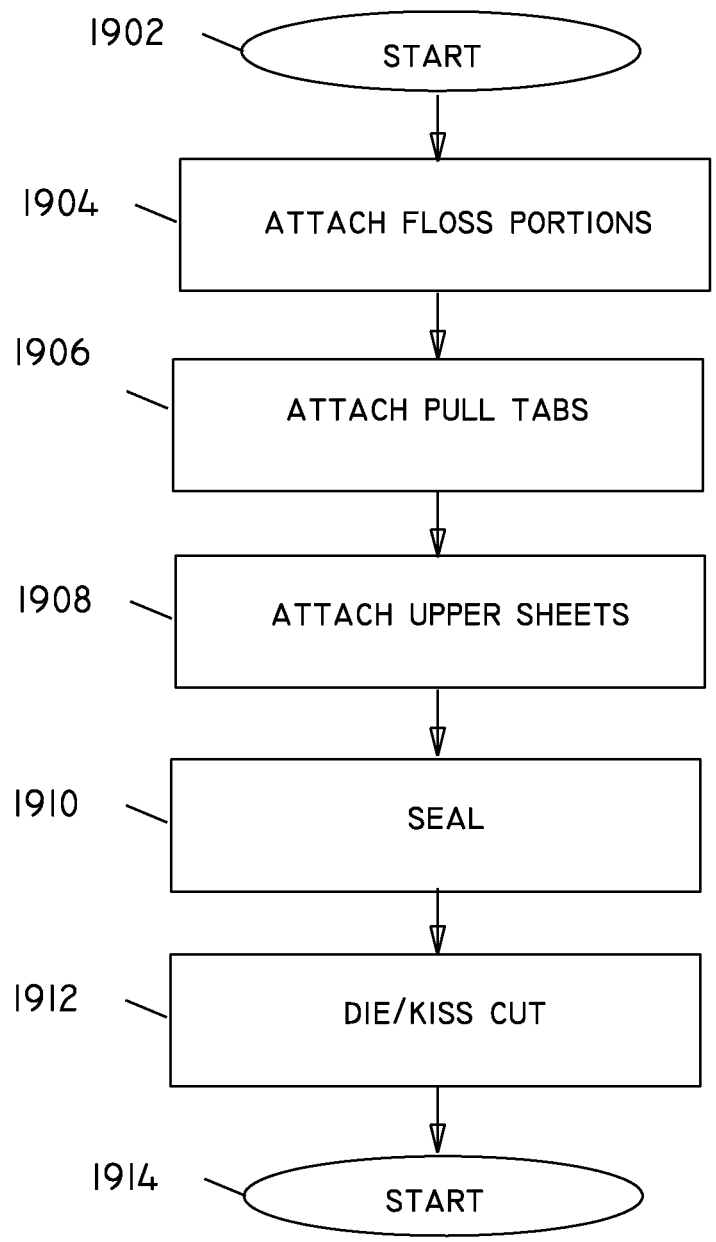
FIG. 19 is a flow chart corresponding to the process performed by an embodiment of the present system.

A process 1900 for forming floss dispensers according to another embodiment of the present system will now be described. A flow chart corresponding to the process 1900 performed by an embodiment of the present system is shown in FIG. 19. The process 1900 may be controlled by one more computers communicating directly and/or over a network. The process 1900 may include one or more of the following steps, acts or operations. Further, one or more of these steps, acts, or operations may be combined and/or separated into sub-steps, sub-acts, or sub-operations, if desired. The process begins during act 1902 and may proceed to act 1904.

During act 1904, floss portions may be attached to lower sheet webbing (e.g., webbing which will form bottom sheets. After performing act 1904, the process continues to act 1906.

During act 1906, the process may optionally attach pull tabs to the bottom webbing and/or individual portions of floss. This act may be skipped when the pull tabs are formed integrally with, the upper and/or Sower sheets. After act 1906, the process may perform act 1908.

During act 1908, the process may attach upper sheet webbing to the lower sheet webbing. The upper sheet webbing may include a plurality of tipper sheets. Similarly, the lower sheet webbing may include a plurality of upper sheets. After act 1908, the process may perform act 1910.

During act 1910, the process may seal the upper sheet webbing to the lower sheet webbing. This may be done applying pressure and/or heat to the combination formed by the upper and/or Sower sheet webbing. After completing act 1910, the process may continue to act 1912.

During act 1912, the process may die/kiss cut the upper and/or Sower sheet webbing to separate dispensers and/or form pull tabs (e.g., when the pull tabs are formed integrally with the upper and/or lower sheets) and or weakened areas. After act 1912, the process may continue to act 1914 where the process may end.

The process 1800 may also include an act of attaching a. reflective layer (or film) to the upper or lower sheets, if desired. This act may occur before and/or after any act of the process 1800.

Figure 20:
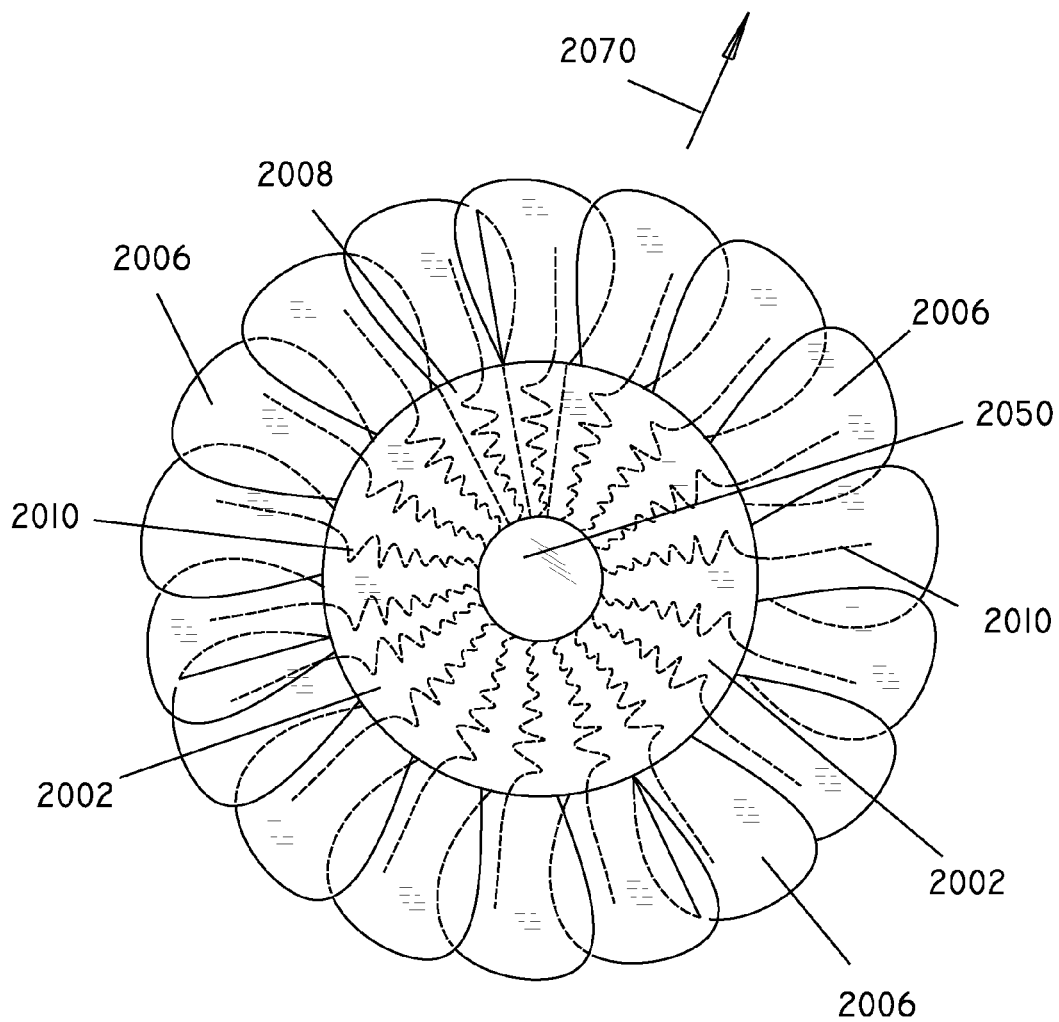
FIG. 20 is a front view of a dispensing system according to still another embodiment of the present system.

FIG. 20 is a front view of a dispensing system 2000 according to still another embodiment of the present system. The dispensing system 2000 may include a plurality of pull tabs 2006 each attached to a lower sheet and/or an upper sheet 2002. A plural of floss portions 2010 may be attached to corresponding ones of the pull tabs 2006. The pull tabs 2002 may be radially arranged so as to form "petals" of a flower pattern. The pull tabs 2002 may include a desired color, pattern, and may be embossed, etc. A reflective surface 2050 may be provided for a user's convenience: The reflective surface 2050 may be provided on the upper sheet 2002 and/or the lower sheet. The pull tabs 2006 may be removed from a corresponding cavity 2008 in which it is located by pulling in the direction of, for example, arrow 2070.

Although the present system has been described with reference to dental floss dispensing system, it is also envisioned that the present system can be extended to other dispensing systems. Accordingly, the present system may be used to dispense tapes, strings, threads, as well as other objects.

Certain additional advantages and features of this invention may be apparent to those skilled in the art upon studying the disclosure, or may be experienced by persons employing the novel system and method of the present invention, chief of which is that a sanitary floss dispensing system and method of operation thereof is provided. Another advantage of the present systems and devices is that a plurality of dispensers may be stacked upon each other or incorporated into a container.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art. without departing from the broader and intended spirit and scope of the present system as set forth in the claims- that follow. Accordingly, the specification and drawings are to be regarded in an illustrative manner and axe not intended to limit the scope of the appended claims.

In interpreting the appended claims, it should be understood that a) the word "comprising" does not exclude the presence of elements or acts other than those listed in a given claim; b) the word "a" or "an" preceding an element does not exclude the presence of a plurality of such elements; c) any reference signs in the claims do not limit their scope; d) several "means" may be represented by the same item or by the same hardware- or software-implemented structure or function; e) any of the disclosed elements may be comprised of hardware portions (e.g., including discrete and integrated electronic circuitry), software portions (e.g., computer programs), and any combination thereof; f) hardware portions may be comprised of one or both of analog and digital portions: g) any of the disclosed devices or portions thereof may be combined or separated into further portions unless specifically stated otherwise; h) no specific sequence of acts or steps is intended to be required including an order of acts depicted In flow diagrams unless specifically indicated; and i) the term "plurality of" an element includes two or more of the claimed element, and does not imply any particular range or number of elements; that is, a plurality of elements may be as few as two elements, and may include an immeasurable number of elements.

What is claimed is:

1. A dental floss dispenser apparatus, comprising:
    first and second sheets at least one of which is corrugated, the corrugated of the at least one of the first and second sheets defining a plurality of channels and ridges, the first and second sheets attached to each other to form a plurality of individually sealed cavities, at least two of the cavities situated between corresponding adjacent ridges of the plurality of ridges and defined by corresponding channels of the plurality of channels, wherein at least two of the plurality of channels have opposed first and second ends which are sealed;
    a plurality of floss portions, each floss portion situated in a corresponding cavity of the plurality of cavities; and
    a plurality of pull tabs at one of the first and second ends and each pull tab attached to a corresponding floss portion of the plurality of floss portions.

2. The dental floss dispenser apparatus of claim 1, further comprising at least one cutout situated between adjacent pull tabs of the plurality of pull tabs, wherein at least part of at least two of the pull tabs is formed from at least one of the first and second sheets which is corrugated.

3. The dental floss dispenser apparatus of claim 1, wherein at least one of the first and second sheets further comprises at least one weakened area at which a corresponding pull tab of the plurality of pull tabs is separated from at least one of the first and second sheets.

4. The dental floss dispenser apparatus of claim 1, wherein each of the plurality of cavities has first and second ends.

5. The dental floss dispenser apparatus of claim 1, wherein the first and second sheets are situated in a curled or folded position.

6. The dental floss dispenser apparatus of claim 5, further comprising an adhesive attached to at least one of the first and second sheets and configured to hold the dispenser apparatus in the curled or folded position.

7. The dental floss dispenser apparatus of claim 1, further comprising a breath strip situated within at least one cavity of the plurality of cavities.

8. A dispenser, comprising:
    first and second sheets at least one of which is corrugated, the corrugated of the at least one of the first and second sheets defining a plurality of channels and ridges, the first and second sheets attached to each other to form a plurality of individually sealed cavities, at least two of the cavities situated between corresponding adjacent ridges of the plurality of ridges and defined by corresponding channels of the plurality of channels, wherein at least two of the plurality of channels have opposed first and second ends which are sealed;
    a plurality of string portions, each string portion situated in a corresponding cavity of the plurality of cavities; and
    a plurality of pull tabs at one of the first and second ends and each pull tab attached to a corresponding string portion of the plurality of string portions.

9. The dispenser of claim 8, further comprising at least one cutout situated between adjacent pull tabs of the plurality of pull tabs.

10. The dispenser of claim 8, wherein at least one of the first and second sheets further comprises at least one weakened area at which a corresponding pull tab of the plurality of pull tabs is separated from at least one of the first and second sheets.

11. The dispenser of claim 8, wherein each of the plurality of cavities has first and second ends.

12. The dispenser of claim 8, wherein the first and second sheets are situated in a curled or folded position.

13. The dispenser of claim 12, further comprising an adhesive attached to at least one of the first and second sheets and configured to hold the dispenser in the curled or folded position.

14. The dispenser of claim 8, further comprising a breath strip situated within at least one cavity of the plurality of cavities.

15. A dental floss dispenser apparatus, comprising:
    a first sheet;
    a second sheet having a plurality of corrugations so as to form a plurality of channels and ridges, the second sheet attached to the first sheet so as to define a plurality of individually sealed cavities situated between corresponding adjacent ridges of the plurality of ridges and defined by corresponding channels of the plurality of channels, wherein at least two of the channels of the plurality of channels have opposed first and second ends which are sealed;
    a plurality of floss portions each floss portion situated in a corresponding cavity of the plurality of cavities; and a plurality of pull tabs at one of the first and second ends and each pull tab attached to a corresponding floss portion of the plurality of floss portions.

16. The dental floss dispenser apparatus of claim 15, further comprising at least one cutout situated between adjacent pull tabs of the plurality of pull tabs.

17. The dental floss dispenser apparatus of claim 15, wherein at least one of the first and second sheets further comprises at least one weakened area at which a corresponding pull tab of the plurality of pull tabs is separated from at least one of the first and second sheets.

18. The dental floss dispenser apparatus of claim 15, wherein each of the plurality of cavities has first and second ends.

19. The dental floss dispenser apparatus of claim 15, wherein the first and second sheets are situated in a curled or folded position.

20. The dental floss dispenser apparatus of claim 19, further comprising an adhesive attached to at least one of the first and second sheets and configured to hold the dispenser apparatus in the curled or folded position.

* * * * *